United States Patent
Johnson

(10) Patent No.: US 9,872,719 B2
(45) Date of Patent: Jan. 23, 2018

(54) SYSTEMS AND METHODS FOR GENERATING ELECTROSURGICAL ENERGY USING A MULTISTAGE POWER CONVERTER

(71) Applicant: COVIDIEN LP, Mansfield, MA (US)

(72) Inventor: Joshua H. Johnson, Arvada, CO (US)

(73) Assignee: COVIDIEN LP, Mansfield, MA (US)

( * ) Notice: Subject to any disclaimer, the term of this patent is extended or adjusted under 35 U.S.C. 154(b) by 606 days.

(21) Appl. No.: 14/179,724

(22) Filed: Feb. 13, 2014

(65) Prior Publication Data

US 2015/0032096 A1 Jan. 29, 2015

Related U.S. Application Data

(60) Provisional application No. 61/858,037, filed on Jul. 24, 2013.

(51) Int. Cl.
*A61B 18/12* (2006.01)
*A61B 18/00* (2006.01)

(52) U.S. Cl.
CPC .. *A61B 18/1206* (2013.01); *A61B 2018/0072* (2013.01); *A61B 2018/00666* (2013.01);
(Continued)

(58) Field of Classification Search
CPC ...... A61B 2018/128; A61B 2018/0072; A61B 2018/1286; A61B 2018/00666;
(Continued)

(56) References Cited

U.S. PATENT DOCUMENTS 1,787,709 A 1/1931 Wappler
1,813,902 A 7/1931 Bovie
(Continued)

FOREIGN PATENT DOCUMENTS

CN 103118614 A 5/2013
DE 179607 C 3/1905
(Continued)

OTHER PUBLICATIONS

US 6,878,148, 04/2005, Goble et al. (withdrawn)
(Continued)

*Primary Examiner* — Jaymi Della
*Assistant Examiner* — Eunhwa Kim

(57) ABSTRACT

The electrosurgical systems and methods according to the present disclosure use a multi-stage power converter for generating electrosurgical energy. The electrosurgical systems include an electrosurgical generator having a power converter coupled to an electrical energy source and configured to generate electrosurgical energy. The power converter includes a boost converter configured to convert a first direct current from the electrical energy source to a second direct current, and a phase-shifted pulse width modulation (PS-PWM) resonant inverter configured to invert the second direct current to an alternating current. The electrosurgical generator also includes a plurality of sensors configured to sense a voltage and a current of the generated electrosurgical energy and a controller coupled to the power converter and the plurality of sensors. The controller includes a signal processor configured to determine tissue impedance based on the sensed voltage and current, and an output controller configured to select one of a plurality of output characteristics based on the determined tissue impedance, and to generate control signals to control the boost converter and the PS-PWM resonant inverter, according to the selected output characteristic.

14 Claims, 10 Drawing Sheets

(52) U.S. Cl.
CPC ............... *A61B 2018/00702* (2013.01); *A61B 2018/00767* (2013.01); *A61B 2018/00827* (2013.01); *A61B 2018/00875* (2013.01); *A61B 2018/00892* (2013.01); *A61B 2018/1286* (2013.01)

(58) Field of Classification Search
CPC   A61B 2018/00892; A61B 2018/00767; A61B 2018/00875; A61B 2018/00827
See application file for complete search history.

(56) References Cited

U.S. PATENT DOCUMENTS

| | | |
|---|---|---|
| 1,841,968 A | 1/1932 | Lowry |
| 1,863,118 A | 6/1932 | Liebel |
| 1,945,867 A | 2/1934 | Rawls |
| 2,693,106 A | 6/1951 | Henry |
| 2,827,056 A | 3/1958 | Degelman |
| 2,849,611 A | 8/1958 | Adams |
| 2,883,198 A | 4/1959 | Narumi |
| 3,001,132 A | 9/1961 | Britt |
| 3,058,470 A | 10/1962 | Seeliger et al. |
| 3,089,496 A | 5/1963 | Degelman |
| 3,154,365 A | 10/1964 | Crimmins |
| 3,163,165 A | 12/1964 | Islikawa |
| 3,252,052 A | 5/1966 | Nash |
| 3,391,351 A | 7/1968 | Trent |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Beierlein |
| 3,743,918 A | 7/1973 | Maitre |
| 3,766,434 A | 10/1973 | Sherman |
| 3,768,019 A | 10/1973 | Podowski |
| 3,768,482 A | 10/1973 | Shaw |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,898,554 A | 8/1975 | Knudsen |
| 3,905,373 A | 9/1975 | Gonser |
| 3,908,176 A | 9/1975 | De Boer et al. |
| 3,913,583 A | 10/1975 | Bross |
| 3,923,063 A | 12/1975 | Andrews et al. |
| 3,933,157 A | 1/1976 | Bjurwill et al. |
| 3,938,072 A | 2/1976 | Baird et al. |
| 3,944,936 A | 3/1976 | Pryor |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 3,998,538 A | 12/1976 | Urso et al. |
| 4,005,714 A | 2/1977 | Hiltebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Lkuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,153,880 A | 5/1979 | Navratil |
| 4,171,700 A | 10/1979 | Farin |
| 4,186,437 A | 1/1980 | Cuk |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gonser |
| 4,204,549 A | 5/1980 | Paglione |
| 4,209,018 A | 6/1980 | Meinke et al. |
| 4,228,809 A | 10/1980 | Paglione |
| 4,229,714 A | 10/1980 | Yu |
| 4,231,372 A | 11/1980 | Newton |
| 4,232,676 A | 11/1980 | Herczog |
| 4,237,887 A | 12/1980 | Gonser |
| 4,247,815 A | 1/1981 | Larsen et al. |
| 4,271,837 A | 6/1981 | Schuler |
| 4,281,373 A | 7/1981 | Mabille |
| 4,287,557 A | 9/1981 | Brehse |
| 4,296,413 A | 10/1981 | Milkovic |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,359,626 A | 11/1982 | Potter |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,430,625 A | 2/1984 | Yokoyama |
| 4,436,091 A | 3/1984 | Banko |
| 4,437,464 A | 3/1984 | Crow |
| 4,438,766 A | 3/1984 | Bowers |
| 4,463,759 A | 8/1984 | Garito et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,524,444 A | 6/1985 | Efron et al. |
| 4,532,924 A | 8/1985 | Auth et al. |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |

(56) References Cited

U.S. PATENT DOCUMENTS

| | | |
|---|---|---|
| 4,572,190 A | 2/1986 | Azam et al. |
| 4,580,575 A | 4/1986 | Birnbaum et al. |
| 4,582,057 A | 4/1986 | Auth et al. |
| 4,586,120 A | 4/1986 | Malik et al. |
| 4,590,934 A | 5/1986 | Malis et al. |
| 4,595,248 A | 6/1986 | Brown |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Paterson |
| 4,644,955 A | 2/1987 | Mioduski |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,741,348 A | 5/1988 | Kikuchi et al. |
| 4,744,372 A | 5/1988 | Kikuchi et al. |
| 4,754,757 A | 7/1988 | Feucht |
| 4,767,999 A | 8/1988 | Verplanck |
| 4,768,969 A | 9/1988 | Bauer et al. |
| 4,785,829 A | 11/1988 | Convert et al. |
| 4,788,634 A | 11/1988 | Schlecht et al. |
| 4,805,621 A | 2/1989 | Heinze et al. |
| 4,818,954 A | 4/1989 | Flachenecker et al. |
| 4,827,927 A | 5/1989 | Newton |
| 4,848,335 A | 7/1989 | Manes |
| 4,860,745 A | 8/1989 | Farin et al. |
| 4,862,889 A | 9/1989 | Feucht |
| 4,887,199 A | 12/1989 | Whittle |
| 4,890,610 A | 1/1990 | Kirwan, Sr. et al. |
| 4,903,696 A | 2/1990 | Stasz et al. |
| 4,907,589 A | 3/1990 | Cosman |
| 4,922,210 A | 5/1990 | Flachenecker et al. |
| 4,925,089 A | 5/1990 | Chaparro et al. |
| 4,931,047 A | 6/1990 | Broadwin et al. |
| 4,931,717 A | 6/1990 | Gray et al. |
| 4,938,761 A | 7/1990 | Ensslin |
| 4,942,313 A | 7/1990 | Kinzel |
| 4,959,606 A | 9/1990 | Forge |
| 4,961,047 A | 10/1990 | Carder |
| 4,961,435 A | 10/1990 | Kitagawa et al. |
| 4,966,597 A | 10/1990 | Cosman |
| 4,969,885 A | 11/1990 | Farin |
| 4,992,719 A | 2/1991 | Harvey |
| 4,993,430 A | 2/1991 | Shimoyama et al. |
| 4,995,877 A | 2/1991 | Ams et al. |
| 5,015,227 A | 5/1991 | Broadwin et al. |
| 5,024,668 A | 6/1991 | Peters et al. |
| 5,044,977 A | 9/1991 | Vindigni |
| 5,057,105 A | 10/1991 | Malone et al. |
| 5,067,953 A | 11/1991 | Feucht |
| 5,075,839 A | 12/1991 | Fisher et al. |
| 5,078,153 A | 1/1992 | Nordlander et al. |
| 5,087,257 A | 2/1992 | Farin et al. |
| 5,099,840 A | 3/1992 | Goble et al. |
| 5,103,804 A | 4/1992 | Abele et al. |
| 5,108,389 A | 4/1992 | Cosmescu |
| 5,108,391 A | 4/1992 | Flachenecker et al. |
| 5,113,116 A | 5/1992 | Wilson |
| 5,119,284 A | 6/1992 | Fisher et al. |
| 5,122,137 A | 6/1992 | Lennox |
| 5,133,711 A | 7/1992 | Hagen |
| 5,151,102 A | 9/1992 | Kamiyama et al. |
| 5,152,762 A | 10/1992 | McElhenney |
| 5,157,603 A | 10/1992 | Scheller et al. |
| 5,160,334 A | 11/1992 | Billings et al. |
| 5,161,893 A | 11/1992 | Shigezawa et al. |
| 5,167,658 A | 12/1992 | Ensslin |
| 5,167,659 A | 12/1992 | Ohtomo et al. |
| 5,190,517 A | 3/1993 | Zieve et al. |
| 5,196,008 A | 3/1993 | Kuenecke et al. |
| 5,196,009 A | 3/1993 | Kirwan, Jr. |
| 5,201,900 A | 4/1993 | Nardella |
| 5,207,691 A | 5/1993 | Nardella |
| 5,216,338 A | 6/1993 | Wilson |
| 5,230,623 A | 7/1993 | Guthrie et al. |
| 5,233,515 A | 8/1993 | Cosman |
| 5,234,427 A | 8/1993 | Ohtomo et al. |
| 5,244,462 A | 9/1993 | Delahuerga et al. |
| 5,249,121 A | 9/1993 | Baum et al. |
| 5,249,585 A | 10/1993 | Turner et al. |
| 5,254,117 A | 10/1993 | Rigby et al. |
| RE34,432 E | 11/1993 | Bertrand |
| 5,267,994 A | 12/1993 | Gentelia et al. |
| 5,267,997 A | 12/1993 | Farin et al. |
| 5,269,780 A | 12/1993 | Roos |
| 5,271,413 A | 12/1993 | Dalamagas et al. |
| 5,281,213 A | 1/1994 | Milder et al. |
| 5,282,840 A | 2/1994 | Hudrlik |
| 5,290,283 A | 3/1994 | Suda |
| 5,295,857 A | 3/1994 | Toly |
| 5,300,068 A | 4/1994 | Rosar et al. |
| 5,300,070 A | 4/1994 | Gentelia et al. |
| 5,304,917 A | 4/1994 | Somerville |
| 5,318,563 A | 6/1994 | Malis et al. |
| 5,323,778 A | 6/1994 | Kandarpa et al. |
| 5,324,283 A | 6/1994 | Heckele |
| 5,330,518 A | 7/1994 | Neilson et al. |
| 5,334,183 A | 8/1994 | Wuchinich |
| 5,334,193 A | 8/1994 | Nardella |
| 5,341,807 A | 8/1994 | Nardella |
| 5,342,356 A | 8/1994 | Ellman et al. |
| 5,342,357 A | 8/1994 | Nardella |
| 5,342,409 A | 8/1994 | Mullett |
| 5,346,406 A | 9/1994 | Hoffman et al. |
| 5,346,491 A | 9/1994 | Oertli |
| 5,348,554 A | 9/1994 | Imran et al. |
| 5,354,325 A | 10/1994 | Chive et al. |
| 5,364,392 A | 11/1994 | Warner et al. |
| 5,369,567 A | 11/1994 | Furuta et al. |
| 5,370,645 A | 12/1994 | Klicek et al. |
| 5,370,672 A | 12/1994 | Fowler et al. |
| 5,370,675 A | 12/1994 | Edwards et al. |
| 5,372,596 A | 12/1994 | Klicek et al. |
| 5,383,874 A | 1/1995 | Jackson et al. |
| 5,383,876 A | 1/1995 | Nardella |
| 5,383,917 A | 1/1995 | Desai et al. |
| 5,385,148 A | 1/1995 | Lesh et al. |
| 5,396,194 A | 3/1995 | Williamson et al. |
| 5,400,267 A | 3/1995 | Denen et al. |
| 5,403,311 A | 4/1995 | Abele et al. |
| 5,403,312 A | 4/1995 | Yates et al. |
| 5,409,000 A | 4/1995 | Imran |
| 5,409,485 A | 4/1995 | Suda |
| 5,413,573 A | 5/1995 | Koivukangas |
| 5,414,238 A | 5/1995 | Steigerwald et al. |
| 5,417,719 A | 5/1995 | Hull et al. |
| 5,422,567 A | 6/1995 | Matsunaga |
| 5,422,926 A | 6/1995 | Smith et al. |
| 5,423,808 A | 6/1995 | Edwards et al. |
| 5,423,809 A | 6/1995 | Klicek |
| 5,423,810 A | 6/1995 | Goble et al. |
| 5,423,811 A | 6/1995 | Imran et al. |
| 5,425,704 A | 6/1995 | Sakurai et al. |
| 5,429,596 A | 7/1995 | Arias et al. |
| 5,430,434 A | 7/1995 | Lederer et al. |
| 5,432,459 A | 7/1995 | Thompson et al. |
| 5,433,739 A | 7/1995 | Sluijter et al. |
| 5,436,566 A | 7/1995 | Thompson et al. |
| 5,438,302 A | 8/1995 | Goble |
| 5,443,462 A | 8/1995 | Hannant |
| 5,443,463 A | 8/1995 | Stern et al. |
| 5,445,635 A | 8/1995 | Denen et al. |
| 5,445,638 A | 8/1995 | Rydell et al. |
| 5,448,466 A | 9/1995 | Erckert |
| 5,451,224 A | 9/1995 | Goble et al. |

(56) References Cited

U.S. PATENT DOCUMENTS

| | | |
|---|---|---|
| 5,452,725 A | 9/1995 | Martenson |
| 5,454,809 A | 10/1995 | Janssen |
| 5,458,597 A | 10/1995 | Edwards et al. |
| 5,462,521 A | 10/1995 | Brucker et al. |
| 5,472,441 A | 12/1995 | Edwards et al. |
| 5,472,443 A | 12/1995 | Cordis et al. |
| 5,474,464 A | 12/1995 | Drewnicki |
| 5,480,399 A | 1/1996 | Hebborn |
| 5,483,952 A | 1/1996 | Aranyi |
| 5,485,312 A | 1/1996 | Horner et al. |
| 5,496,312 A | 3/1996 | Klicek |
| 5,496,313 A | 3/1996 | Gentelia et al. |
| 5,496,314 A | 3/1996 | Eggers |
| 5,498,261 A | 3/1996 | Strul |
| 5,500,012 A | 3/1996 | Brucker et al. |
| 5,500,616 A | 3/1996 | Ochi |
| 5,511,993 A | 4/1996 | Yamada et al. |
| 5,514,129 A | 5/1996 | Smith |
| 5,520,684 A | 5/1996 | Imran |
| 5,531,774 A | 7/1996 | Schulman et al. |
| 5,534,018 A | 7/1996 | Wahlstrand et al. |
| 5,536,267 A | 7/1996 | Edwards et al. |
| 5,539,630 A | 7/1996 | Pietkiewicz et al. |
| 5,540,677 A | 7/1996 | Sinofsky |
| 5,540,681 A | 7/1996 | Strul et al. |
| 5,540,682 A | 7/1996 | Gardner et al. |
| 5,540,683 A | 7/1996 | Ichikawa et al. |
| 5,540,684 A | 7/1996 | Hassler, Jr. |
| 5,541,376 A | 7/1996 | Ladtkow et al. |
| 5,542,916 A | 8/1996 | Hirsch et al. |
| 5,545,161 A | 8/1996 | Imran |
| 5,554,172 A | 9/1996 | Homer et al. |
| 5,556,396 A | 9/1996 | Cohen et al. |
| 5,558,671 A | 9/1996 | Yates |
| 5,559,688 A | 9/1996 | Pringle |
| 5,562,720 A | 10/1996 | Stern et al. |
| 5,569,242 A | 10/1996 | Lax et al. |
| 5,571,147 A | 11/1996 | Sludter et al. |
| 5,573,533 A | 11/1996 | Strul |
| 5,584,830 A | 12/1996 | Ladd et al. |
| 5,588,432 A | 12/1996 | Crowley |
| 5,596,466 A | 1/1997 | Ochi |
| 5,596,995 A | 1/1997 | Sherman et al. |
| 5,599,344 A | 2/1997 | Paterson |
| 5,599,345 A | 2/1997 | Edwards et al. |
| 5,599,348 A | 2/1997 | Gentelia et al. |
| 5,605,150 A | 2/1997 | Radons et al. |
| 5,609,560 A | 3/1997 | Ichikawa et al. |
| 5,613,966 A | 3/1997 | Makower et al. |
| 5,620,481 A | 4/1997 | Desai et al. |
| 5,626,575 A | 5/1997 | Crenner |
| 5,628,745 A | 5/1997 | Bek |
| 5,628,771 A | 5/1997 | Mizukawa et al. |
| 5,633,578 A | 5/1997 | Eggers et al. |
| 5,640,113 A | 6/1997 | Hu |
| 5,643,330 A | 7/1997 | Holsheimer et al. |
| 5,647,869 A | 7/1997 | Goble et al. |
| 5,647,871 A | 7/1997 | Levine et al. |
| 5,651,780 A | 7/1997 | Jackson et al. |
| 5,658,322 A | 8/1997 | Fleming |
| 5,660,567 A | 8/1997 | Nierlich et al. |
| 5,664,953 A | 9/1997 | Reylek |
| 5,674,217 A | 10/1997 | Wahlstrom et al. |
| 5,675,609 A | 10/1997 | Johnson |
| 5,678,568 A | 10/1997 | Uchikubo et al. |
| 5,681,307 A | 10/1997 | McMahan |
| 5,685,840 A | 11/1997 | Schechter et al. |
| 5,688,267 A | 11/1997 | Panescu et al. |
| 5,693,042 A | 12/1997 | Boiarski et al. |
| 5,693,078 A | 12/1997 | Desai et al. |
| 5,693,082 A | 12/1997 | Warner et al. |
| 5,694,304 A | 12/1997 | Telefus et al. |
| 5,695,494 A | 12/1997 | Becker |
| 5,696,441 A | 12/1997 | Mak et al. |
| 5,697,925 A | 12/1997 | Taylor |
| 5,697,927 A | 12/1997 | Imran et al. |
| 5,702,386 A | 12/1997 | Stern et al. |
| 5,702,429 A | 12/1997 | King |
| 5,707,369 A | 1/1998 | Vaitekunas et al. |
| 5,712,772 A | 1/1998 | Telefus et al. |
| 5,713,896 A | 2/1998 | Nardella |
| 5,718,246 A | 2/1998 | Vona |
| 5,720,742 A | 2/1998 | Zacharias |
| 5,720,744 A | 2/1998 | Eggleston et al. |
| 5,722,975 A | 3/1998 | Edwards et al. |
| 5,729,448 A | 3/1998 | Haynie et al. |
| 5,733,281 A | 3/1998 | Nardella |
| 5,735,846 A | 4/1998 | Panescu et al. |
| 5,738,683 A | 4/1998 | Osypka |
| 5,743,900 A | 4/1998 | Hara |
| 5,743,903 A | 4/1998 | Stern et al. |
| 5,749,869 A | 5/1998 | Lindenmeier et al. |
| 5,749,871 A | 5/1998 | Hood et al. |
| 5,755,715 A | 5/1998 | Stern et al. |
| 5,762,609 A | 6/1998 | Benaron et al. |
| 5,766,153 A | 6/1998 | Eggers et al. |
| 5,766,165 A | 6/1998 | Gentelia et al. |
| 5,769,847 A | 6/1998 | Panescu et al. |
| 5,772,659 A | 6/1998 | Becker et al. |
| 5,777,519 A | 7/1998 | Simopoulos |
| 5,788,688 A | 8/1998 | Bauer et al. |
| 5,792,138 A | 8/1998 | Shipp |
| 5,797,902 A | 8/1998 | Netherly |
| 5,797,941 A | 8/1998 | Schulze et al. |
| 5,807,253 A | 9/1998 | Dumoulin et al. |
| 5,810,804 A | 9/1998 | Gough et al. |
| 5,814,092 A | 9/1998 | King |
| 5,817,091 A | 10/1998 | Nardella et al. |
| 5,817,093 A | 10/1998 | Williamson, IV et al. |
| 5,820,568 A | 10/1998 | Willis |
| 5,827,271 A | 10/1998 | Buysse et al. |
| 5,830,212 A | 11/1998 | Cartmell et al. |
| 5,831,166 A | 11/1998 | Kozuka et al. |
| 5,836,909 A | 11/1998 | Cosmescu |
| 5,836,943 A | 11/1998 | Miller, III |
| 5,836,990 A | 11/1998 | Li |
| 5,843,019 A | 12/1998 | Eggers et al. |
| 5,843,075 A | 12/1998 | Taylor |
| 5,846,236 A | 12/1998 | Lindenmeier et al. |
| 5,849,010 A | 12/1998 | Wurzer et al. |
| 5,853,409 A | 12/1998 | Swanson et al. |
| 5,860,832 A | 1/1999 | Wayt et al. |
| 5,865,788 A | 2/1999 | Edwards et al. |
| 5,868,737 A | 2/1999 | Taylor et al. |
| 5,868,739 A | 2/1999 | Lindenmeier et al. |
| 5,868,740 A | 2/1999 | LeVeen et al. |
| 5,871,481 A | 2/1999 | Kannenberg et al. |
| 5,891,142 A | 4/1999 | Eggers et al. |
| 5,893,848 A | 4/1999 | Negus et al. |
| 5,897,552 A | 4/1999 | Edwards et al. |
| 5,906,614 A | 5/1999 | Stern et al. |
| 5,907,223 A * | 5/1999 | Gu .................. H02M 1/4208 315/247 |
| 5,908,444 A | 6/1999 | Azure |
| 5,913,882 A | 6/1999 | King |
| 5,921,982 A | 7/1999 | Lesh et al. |
| 5,925,070 A | 7/1999 | King et al. |
| 5,931,835 A | 8/1999 | MacKey |
| 5,931,836 A | 8/1999 | Haifa et al. |
| 5,935,124 A | 8/1999 | Klumb et al. |
| 5,936,446 A | 8/1999 | Lee |
| 5,938,690 A | 8/1999 | Law et al. |
| 5,944,553 A | 8/1999 | Yasui et al. |
| 5,948,007 A | 9/1999 | Starkebaum et al. |
| 5,951,545 A | 9/1999 | Schilling et al. |
| 5,951,546 A | 9/1999 | Lorentzen |
| 5,954,686 A | 9/1999 | Garito et al. |
| 5,954,717 A | 9/1999 | Behl et al. |
| 5,954,719 A | 9/1999 | Chen et al. |
| 5,957,961 A | 9/1999 | Maguire et al. |
| 5,957,969 A | 9/1999 | Warner et al. |
| 5,959,253 A | 9/1999 | Shinchi |
| 5,961,344 A | 10/1999 | Rosales et al. |
| 5,961,871 A | 10/1999 | Bible et al. |

(56) References Cited

U.S. PATENT DOCUMENTS

| | | |
|---|---|---|
| 5,964,746 A | 10/1999 | McCary |
| 5,971,980 A | 10/1999 | Sherman |
| 5,971,981 A | 10/1999 | Hill et al. |
| 5,976,128 A | 11/1999 | Schilling et al. |
| 5,983,141 A | 11/1999 | Sluijter et al. |
| 5,999,848 A | 12/1999 | Gord et al. |
| 6,002,968 A | 12/1999 | Edwards |
| 6,007,532 A | 12/1999 | Netherly |
| 6,010,499 A | 1/2000 | Cobb |
| 6,013,074 A | 1/2000 | Taylor |
| 6,014,581 A | 1/2000 | Whayne et al. |
| 6,017,338 A | 1/2000 | Brucker et al. |
| 6,017,354 A | 1/2000 | Culp et al. |
| 6,022,346 A | 2/2000 | Panescu et al. |
| 6,022,347 A | 2/2000 | Lindenmeier et al. |
| 6,033,399 A | 3/2000 | Gines |
| 6,039,731 A | 3/2000 | Taylor et al. |
| 6,039,732 A | 3/2000 | Ichikawa et al. |
| 6,041,260 A | 3/2000 | Stern et al. |
| 6,044,283 A | 3/2000 | Fein et al. |
| 6,045,527 A | 4/2000 | Appelbaum et al. |
| 6,053,910 A | 4/2000 | Fleenor |
| 6,053,912 A | 4/2000 | Panescu et al. |
| 6,055,458 A | 4/2000 | Cochran et al. |
| 6,056,745 A | 5/2000 | Panescu et al. |
| 6,056,746 A | 5/2000 | Goble et al. |
| 6,059,780 A | 5/2000 | Gough et al. |
| 6,059,781 A | 5/2000 | Yamanashi et al. |
| 6,063,075 A | 5/2000 | Mihori |
| 6,063,078 A | 5/2000 | Wittkampf |
| 6,066,137 A | 5/2000 | Greep |
| 6,068,627 A | 5/2000 | Orszulak et al. |
| 6,074,089 A | 6/2000 | Hollander et al. |
| 6,074,386 A | 6/2000 | Goble et al. |
| 6,074,388 A | 6/2000 | Tockweller et al. |
| 6,080,149 A | 6/2000 | Huang et al. |
| 6,088,614 A | 7/2000 | Swanson |
| 6,089,864 A | 7/2000 | Buckner et al. |
| 6,090,123 A | 7/2000 | Culp et al. |
| 6,093,186 A | 7/2000 | Goble |
| 6,102,497 A | 8/2000 | Ehr et al. |
| 6,102,907 A | 8/2000 | Smethers et al. |
| 6,104,248 A | 8/2000 | Carver |
| 6,106,524 A | 8/2000 | Eggers et al. |
| 6,113,591 A | 9/2000 | Whayne et al. |
| 6,113,592 A | 9/2000 | Taylor |
| 6,113,593 A | 9/2000 | Tu et al. |
| 6,113,596 A | 9/2000 | Hooven et al. |
| 6,123,701 A | 9/2000 | Nezhat |
| 6,123,702 A | 9/2000 | Swanson et al. |
| 6,132,429 A | 10/2000 | Baker |
| 6,139,349 A | 10/2000 | Wright |
| 6,142,992 A | 11/2000 | Cheng et al. |
| 6,144,937 A | 11/2000 | Ali |
| 6,155,975 A | 12/2000 | Urich et al. |
| 6,162,184 A | 12/2000 | Swanson et al. |
| 6,162,217 A | 12/2000 | Kannenberg et al. |
| 6,165,169 A | 12/2000 | Panescu et al. |
| 6,165,173 A | 12/2000 | Kamdar et al. |
| 6,171,304 B1 | 1/2001 | Netherly |
| 6,173,713 B1 | 1/2001 | Dawson |
| 6,183,468 B1 | 2/2001 | Swanson et al. |
| 6,186,147 B1 | 2/2001 | Cobb |
| 6,188,211 B1 | 2/2001 | Rincon-Mora et al. |
| 6,193,713 B1 | 2/2001 | Geistert et al. |
| 6,197,023 B1 | 3/2001 | Muntermann |
| 6,198,642 B1 | 3/2001 | Kociecki |
| 6,200,314 B1 | 3/2001 | Sherman |
| 6,203,541 B1 | 3/2001 | Keppel |
| 6,210,403 B1 | 4/2001 | Klicek |
| 6,216,704 B1 | 4/2001 | Ingle et al. |
| 6,222,356 B1 | 4/2001 | Taghizadeh-Kaschani |
| 6,228,078 B1 | 5/2001 | Eggers et al. |
| 6,228,080 B1 | 5/2001 | Gines |
| 6,228,081 B1 | 5/2001 | Goble |
| 6,231,569 B1 | 5/2001 | Bek et al. |
| 6,232,556 B1 | 5/2001 | Daugherty et al. |
| 6,235,020 B1 | 5/2001 | Cheng et al. |
| 6,235,022 B1 | 5/2001 | Hallock et al. |
| 6,237,604 B1 | 5/2001 | Burnside et al. |
| 6,238,387 B1 | 5/2001 | Miller, III |
| 6,238,388 B1 | 5/2001 | Ellman et al. |
| 6,241,723 B1 | 6/2001 | Heim et al. |
| 6,241,725 B1 | 6/2001 | Cosman |
| 6,243,654 B1 | 6/2001 | Johnson et al. |
| 6,245,061 B1 | 6/2001 | Panescu et al. |
| 6,245,063 B1 | 6/2001 | Uphoff |
| 6,245,065 B1 | 6/2001 | Panescu et al. |
| 6,246,912 B1 | 6/2001 | Sluijter et al. |
| 6,251,106 B1 | 6/2001 | Becker et al. |
| 6,254,422 B1 | 7/2001 | Feye-Hohmann |
| 6,258,085 B1 | 7/2001 | Eggleston |
| 6,259,937 B1 | 7/2001 | Schulman et al. |
| 6,261,285 B1 | 7/2001 | Novak et al. |
| 6,261,286 B1 | 7/2001 | Goble et al. |
| 6,267,760 B1 | 7/2001 | Swanson |
| 6,270,497 B1 | 8/2001 | Sekino et al. |
| 6,273,886 B1 | 8/2001 | Edwards et al. |
| 6,275,786 B1 | 8/2001 | Daners |
| 6,287,304 B1 | 9/2001 | Eggers et al. |
| 6,293,941 B1 | 9/2001 | Strul et al. |
| 6,293,942 B1 | 9/2001 | Goble et al. |
| 6,293,943 B1 | 9/2001 | Panescu et al. |
| 6,296,636 B1 | 10/2001 | Cheng et al. |
| 6,304,138 B1 | 10/2001 | Johnson |
| 6,306,131 B1 | 10/2001 | Hareyama et al. |
| 6,306,134 B1 | 10/2001 | Goble et al. |
| 6,309,386 B1 | 10/2001 | Bek |
| 6,322,558 B1 | 11/2001 | Taylor et al. |
| 6,325,799 B1 | 12/2001 | Goble |
| 6,329,778 B1 | 12/2001 | Culp et al. |
| 6,337,998 B1 | 1/2002 | Behl et al. |
| 6,338,657 B1 | 1/2002 | Harper et al. |
| 6,341,981 B1 | 1/2002 | Gorman |
| 6,350,262 B1 | 2/2002 | Ashley |
| 6,350,263 B1 | 2/2002 | Wetzig et al. |
| 6,358,245 B1 | 3/2002 | Edwards et al. |
| 6,364,877 B1 | 4/2002 | Goble et al. |
| 6,370,408 B1 | 4/2002 | Merchant et al. |
| 6,371,963 B1 | 4/2002 | Nishtala et al. |
| 6,383,183 B1 | 5/2002 | Sekino et al. |
| 6,387,092 B1 | 5/2002 | Burnside et al. |
| 6,391,024 B1 | 5/2002 | Sun et al. |
| 6,398,779 B1 | 6/2002 | Buysse et al. |
| 6,398,781 B1 | 6/2002 | Goble et al. |
| 6,402,741 B1 | 6/2002 | Keppel et al. |
| 6,402,742 B1 | 6/2002 | Blewett et al. |
| 6,402,743 B1 | 6/2002 | Orszulak et al. |
| 6,402,748 B1 | 6/2002 | Schoenman et al. |
| 6,409,722 B1 | 6/2002 | Hoey et al. |
| 6,413,256 B1 | 7/2002 | Truckai et al. |
| 6,416,509 B1 | 7/2002 | Goble et al. |
| 6,422,896 B2 | 7/2002 | Aoki et al. |
| 6,423,057 B1 | 7/2002 | He et al. |
| 6,424,186 B1 | 7/2002 | Quimby et al. |
| 6,426,886 B1 | 7/2002 | Goder |
| 6,427,089 B1 | 7/2002 | Knowlton |
| 6,428,537 B1 | 8/2002 | Swanson et al. |
| 6,436,096 B1 | 8/2002 | Hareyama |
| 6,440,157 B1 | 8/2002 | Shigezawa et al. |
| 6,451,015 B1 | 9/2002 | Rittman, III et al. |
| 6,454,594 B2 | 9/2002 | Sawayanagi |
| 6,458,121 B1 | 10/2002 | Rosenstock et al. |
| 6,458,122 B1 | 10/2002 | Pozzato |
| 6,464,689 B1 | 10/2002 | Qin et al. |
| 6,464,696 B1 | 10/2002 | Oyama et al. |
| 6,468,270 B1 | 10/2002 | Hovda et al. |
| 6,468,273 B1 | 10/2002 | Leveen et al. |
| 6,469,481 B1 | 10/2002 | Tateishi |
| 6,482,201 B1 | 11/2002 | Olsen et al. |
| 6,485,487 B1 | 11/2002 | Sherman |
| 6,488,678 B2 | 12/2002 | Sherman |
| 6,494,880 B1 | 12/2002 | Swanson et al. |
| 6,497,659 B1 | 12/2002 | Rafert |

(56) References Cited

U.S. PATENT DOCUMENTS

| | | |
|---|---|---|
| 6,498,466 B1 | 12/2002 | Edwards |
| 6,506,189 B1 | 1/2003 | Rittman, III et al. |
| 6,508,815 B1 | 1/2003 | Strul et al. |
| 6,511,476 B2 | 1/2003 | Hareyama |
| 6,511,478 B1 | 1/2003 | Burnside et al. |
| 6,514,251 B1 | 2/2003 | Ni et al. |
| 6,517,538 B1 | 2/2003 | Jacob et al. |
| 6,522,931 B2 | 2/2003 | Manker et al. |
| 6,524,308 B1 | 2/2003 | Muller et al. |
| 6,537,272 B2 | 3/2003 | Christopherson et al. |
| 6,544,258 B2 | 4/2003 | Fleenor et al. |
| 6,544,260 B1 | 4/2003 | Markel et al. |
| 6,546,270 B1 | 4/2003 | Goldin et al. |
| 6,547,786 B1 | 4/2003 | Goble |
| 6,557,559 B1 | 5/2003 | Eggers et al. |
| 6,558,376 B2 | 5/2003 | Bishop |
| 6,558,377 B2 | 5/2003 | Lee et al. |
| 6,560,470 B1 | 5/2003 | Pologe |
| 6,562,037 B2 | 5/2003 | Paton et al. |
| 6,565,559 B2 | 5/2003 | Eggleston |
| 6,565,562 B1 | 5/2003 | Shah et al. |
| 6,575,969 B1 | 6/2003 | Rittman, III et al. |
| 6,578,579 B2 | 6/2003 | Burnside et al. |
| 6,579,288 B1 | 6/2003 | Swanson et al. |
| 6,582,427 B1 | 6/2003 | Goble et al. |
| 6,602,243 B2 | 8/2003 | Noda |
| 6,602,252 B2 | 8/2003 | Mollenauer |
| 6,611,793 B1 | 8/2003 | Burnside et al. |
| 6,620,157 B1 | 9/2003 | Dabney et al. |
| 6,620,189 B1 | 9/2003 | Machold et al. |
| 6,623,423 B2 | 9/2003 | Sakurai et al. |
| 6,626,901 B1 | 9/2003 | Treat et al. |
| 6,629,973 B1 | 10/2003 | Wågrdell et al. |
| 6,629,974 B2 | 10/2003 | Penny et al. |
| 6,632,193 B1 | 10/2003 | Davison et al. |
| 6,635,056 B2 | 10/2003 | Kadhiresan et al. |
| 6,635,057 B2 | 10/2003 | Harano et al. |
| 6,645,198 B1 | 11/2003 | Bommannan et al. |
| 6,648,883 B2 | 11/2003 | Francischelli et al. |
| 6,651,669 B1 | 11/2003 | Burnside |
| 6,652,513 B2 | 11/2003 | Panescu et al. |
| 6,652,514 B2 | 11/2003 | Ellman et al. |
| 6,653,569 B1 | 11/2003 | Sung |
| 6,656,177 B2 | 12/2003 | Truckai et al. |
| 6,663,623 B1 | 12/2003 | Oyama et al. |
| 6,663,624 B2 | 12/2003 | Edwards et al. |
| 6,663,627 B2 | 12/2003 | Francischelli et al. |
| 6,666,860 B1 | 12/2003 | Takahashi |
| 6,672,151 B1 | 1/2004 | Schultz et al. |
| 6,679,875 B2 | 1/2004 | Honda et al. |
| 6,682,527 B2 | 1/2004 | Strul |
| 6,685,700 B2 | 2/2004 | Behl et al. |
| 6,685,701 B2 | 2/2004 | Orszulak et al. |
| 6,685,703 B2 | 2/2004 | Pearson et al. |
| 6,689,131 B2 | 2/2004 | McClurken |
| 6,692,489 B1 | 2/2004 | Heim et al. |
| 6,693,782 B1 | 2/2004 | Lash |
| 6,695,837 B2 | 2/2004 | Howell |
| 6,696,844 B2 | 2/2004 | Wong et al. |
| 6,700,076 B2 | 3/2004 | Sun et al. |
| 6,712,813 B2 | 3/2004 | Ellman et al. |
| 6,723,091 B2 | 4/2004 | Goble et al. |
| 6,730,078 B2 | 5/2004 | Simpson et al. |
| 6,730,079 B2 | 5/2004 | Lovewell |
| 6,730,080 B2 | 5/2004 | Harano et al. |
| 6,733,495 B1 | 5/2004 | Bek et al. |
| 6,733,498 B2 | 5/2004 | Paton et al. |
| 6,736,810 B2 | 5/2004 | Hoey et al. |
| 6,740,079 B1 | 5/2004 | Eggers et al. |
| 6,740,085 B2 | 5/2004 | Hareyama et al. |
| 6,743,225 B2 | 6/2004 | Sanchez et al. |
| 6,746,284 B1 | 6/2004 | Spink, Jr. |
| 6,749,624 B2 | 6/2004 | Knowlton |
| 6,755,825 B2 | 6/2004 | Shoenman et al. |
| 6,758,846 B2 | 7/2004 | Goble et al. |
| 6,761,716 B2 | 7/2004 | Kadhiresan et al. |
| 6,775,575 B2 | 8/2004 | Bommannan et al. |
| 6,778,044 B2 | 8/2004 | Fehrenbach et al. |
| 6,783,523 B2 | 8/2004 | Qin et al. |
| 6,784,405 B2 | 8/2004 | Flugstad et al. |
| 6,786,905 B2 | 9/2004 | Swanson et al. |
| 6,788,977 B2 | 9/2004 | Fenn et al. |
| 6,790,206 B2 | 9/2004 | Panescu |
| 6,792,390 B1 | 9/2004 | Burnside et al. |
| 6,796,980 B2 | 9/2004 | Hall |
| 6,796,981 B2 | 9/2004 | Wham et al. |
| 6,809,508 B2 | 10/2004 | Donofrio |
| 6,818,000 B2 | 11/2004 | Muller et al. |
| 6,819,027 B2 | 11/2004 | Saraf |
| 6,824,539 B2 | 11/2004 | Novak |
| 6,830,569 B2 | 12/2004 | Thompson et al. |
| 6,837,888 B2 | 1/2005 | Ciarrocca et al. |
| 6,843,682 B2 | 1/2005 | Matsuda et al. |
| 6,843,789 B2 | 1/2005 | Goble |
| 6,849,073 B2 | 2/2005 | Hoey et al. |
| 6,855,141 B2 | 2/2005 | Lovewell |
| 6,855,142 B2 | 2/2005 | Harano et al. |
| 6,860,881 B2 | 3/2005 | Sturm et al. |
| 6,864,686 B2 | 3/2005 | Novak et al. |
| 6,875,210 B2 | 4/2005 | Refior et al. |
| 6,887,240 B1 | 5/2005 | Lands et al. |
| 6,890,331 B2 | 5/2005 | Kristensen |
| 6,893,435 B2 | 5/2005 | Goble |
| 6,899,538 B2 | 5/2005 | Matoba |
| 6,923,804 B2 | 8/2005 | Eggers et al. |
| 6,929,641 B2 | 8/2005 | Goble et al. |
| 6,936,047 B2 | 8/2005 | Nasab et al. |
| 6,939,344 B2 | 9/2005 | Kreindel |
| 6,939,346 B2 | 9/2005 | Kannenberg et al. |
| 6,939,347 B2 | 9/2005 | Thompson |
| 6,942,660 B2 | 9/2005 | Pantera et al. |
| 6,948,503 B2 | 9/2005 | Refior et al. |
| 6,953,461 B2 | 10/2005 | McClurken et al. |
| 6,958,064 B2 | 10/2005 | Rioux et al. |
| 6,962,587 B2 | 11/2005 | Johnson et al. |
| 6,966,907 B2 | 11/2005 | Goble |
| 6,970,752 B1 | 11/2005 | Lim et al. |
| 6,974,453 B2 | 12/2005 | Woloszko et al. |
| 6,974,463 B2 | 12/2005 | Magers et al. |
| 6,977,495 B2 | 12/2005 | Donofrio |
| 6,979,329 B2 | 12/2005 | Burnside et al. |
| 6,984,231 B2 | 1/2006 | Goble et al. |
| 6,989,010 B2 | 1/2006 | Francischelli et al. |
| 6,994,704 B2 | 2/2006 | Qin et al. |
| 6,994,707 B2 | 2/2006 | Ellman et al. |
| 6,997,935 B2 | 2/2006 | Anderson et al. |
| 7,001,379 B2 | 2/2006 | Behl et al. |
| 7,001,381 B2 | 2/2006 | Harano et al. |
| 7,004,174 B2 | 2/2006 | Eggers et al. |
| 7,008,369 B2 | 3/2006 | Cuppen |
| 7,008,417 B2 | 3/2006 | Eick |
| 7,008,421 B2 | 3/2006 | Daniel et al. |
| 7,025,764 B2 | 4/2006 | Paton et al. |
| 7,033,351 B2 | 4/2006 | Howell |
| 7,041,096 B2 | 5/2006 | Malis et al. |
| 7,044,948 B2 | 5/2006 | Keppel |
| 7,044,949 B2 | 5/2006 | Orszulak et al. |
| 7,048,687 B1 | 5/2006 | Reuss et al. |
| 7,058,372 B1 | 6/2006 | Pardoen et al. |
| 7,060,063 B2 | 6/2006 | Marion et al. |
| 7,062,331 B2 | 6/2006 | Zarinetchi et al. |
| 7,063,692 B2 | 6/2006 | Sakurai et al. |
| 7,066,933 B2 | 6/2006 | Hagg |
| 7,074,217 B2 | 7/2006 | Strul et al. |
| 7,083,618 B2 | 8/2006 | Couture et al. |
| 7,087,054 B2 | 8/2006 | Truckai et al. |
| 7,094,231 B1 | 8/2006 | Ellman et al. |
| 7,104,834 B2 | 9/2006 | Robinson et al. |
| RE39,358 E | 10/2006 | Goble |
| 7,115,121 B2 | 10/2006 | Novak |
| 7,115,124 B1 | 10/2006 | Xiao |
| 7,118,564 B2 | 10/2006 | Ritchie et al. |
| 7,122,031 B2 | 10/2006 | Edwards et al. |
| 7,131,445 B2 | 11/2006 | Amoah |

(56) References Cited

U.S. PATENT DOCUMENTS

| | | |
|---|---|---|
| 7,131,860 B2 | 11/2006 | Sartor et al. |
| 7,137,980 B2 | 11/2006 | Buysse et al. |
| 7,146,210 B2 | 12/2006 | Palti |
| 7,147,638 B2 | 12/2006 | Chapman et al. |
| 7,151,964 B2 | 12/2006 | Desai et al. |
| 7,153,300 B2 | 12/2006 | Goble |
| 7,156,842 B2 | 1/2007 | Sartor et al. |
| 7,156,844 B2 | 1/2007 | Reschke et al. |
| 7,156,846 B2 | 1/2007 | Dycus et al. |
| 7,160,293 B2 | 1/2007 | Sturm et al. |
| 7,163,536 B2 | 1/2007 | Godara |
| 7,166,986 B2 | 1/2007 | Kendall |
| 7,169,144 B2 | 1/2007 | Hoey et al. |
| 7,172,591 B2 | 2/2007 | Harano et al. |
| 7,175,618 B2 | 2/2007 | Dabney et al. |
| 7,175,621 B2 | 2/2007 | Heim et al. |
| 7,184,820 B2 | 2/2007 | Jersey-Willuhn et al. |
| 7,190,933 B2 | 3/2007 | De Ruijter et al. |
| 7,192,427 B2 | 3/2007 | Chapelon et al. |
| 7,195,627 B2 | 3/2007 | Amoah et al. |
| 7,200,010 B2 | 4/2007 | Broman et al. |
| 7,203,556 B2 | 4/2007 | Daners |
| 7,204,835 B2 | 4/2007 | Latterell et al. |
| 7,211,081 B2 | 5/2007 | Goble |
| 7,214,224 B2 | 5/2007 | Goble |
| 7,217,269 B2 | 5/2007 | Ei-Galley et al. |
| 7,220,260 B2 | 5/2007 | Fleming et al. |
| 7,223,264 B2 | 5/2007 | Daniel et al. |
| 7,226,447 B2 | 6/2007 | Uchida et al. |
| 7,229,469 B1 | 6/2007 | Witzel et al. |
| 7,232,437 B2 | 6/2007 | Berman et al. |
| 7,233,278 B2 | 6/2007 | Eriksson |
| 7,238,181 B2 | 7/2007 | Daners et al. |
| 7,238,183 B2 | 7/2007 | Kreindel |
| 7,241,296 B2 | 7/2007 | Buysse et al. |
| 7,244,255 B2 | 7/2007 | Daners et al. |
| 7,247,155 B2 | 7/2007 | Hoey et al. |
| 7,250,048 B2 | 7/2007 | Francischelli et al. |
| 7,250,746 B2 | 7/2007 | Oswald et al. |
| 7,255,694 B2 | 8/2007 | Keppel |
| 7,258,688 B1 | 8/2007 | Shah et al. |
| 7,269,034 B2 | 9/2007 | Schlecht |
| 7,276,068 B2 | 10/2007 | Johnson et al. |
| 7,282,048 B2 | 10/2007 | Goble et al. |
| 7,282,049 B2 | 10/2007 | Orszulak et al. |
| 7,285,117 B2 | 10/2007 | Krueger et al. |
| 7,294,127 B2 | 11/2007 | Leung et al. |
| 7,300,435 B2 | 11/2007 | Wham et al. |
| 7,300,437 B2 | 11/2007 | Pozzato |
| 7,303,557 B2 | 12/2007 | Wham et al. |
| 7,305,311 B2 | 12/2007 | van Zyl |
| 7,311,703 B2 | 12/2007 | Turovskiy et al. |
| 7,316,682 B2 | 1/2008 | Konesky |
| 7,317,954 B2 | 1/2008 | McGreevy |
| 7,317,955 B2 | 1/2008 | McGreevy |
| 7,324,357 B2 | 1/2008 | Miura et al. |
| 7,333,859 B2 | 2/2008 | Rinaldi et al. |
| 7,341,586 B2 | 3/2008 | Daniel et al. |
| 7,344,532 B2 | 3/2008 | Goble et al. |
| 7,353,068 B2 | 4/2008 | Tanaka et al. |
| 7,354,436 B2 | 4/2008 | Rioux et al. |
| 7,357,800 B2 | 4/2008 | Swanson |
| 7,364,577 B2 | 4/2008 | Wham et al. |
| 7,364,578 B2 | 4/2008 | Francischelli et al. |
| 7,364,972 B2 | 4/2008 | Ono et al. |
| 7,367,972 B2 | 5/2008 | Francischelli et al. |
| RE40,388 E | 6/2008 | Gines |
| 7,396,336 B2 | 7/2008 | Orszulak et al. |
| 7,402,754 B2 | 7/2008 | Kirwan, Jr. et al. |
| D574,323 S | 8/2008 | Waaler |
| 7,407,502 B2 | 8/2008 | Strul et al. |
| 7,416,437 B2 | 8/2008 | Sartor et al. |
| 7,416,549 B2 | 8/2008 | Young et al. |
| 7,422,582 B2 | 9/2008 | Malackowski et al. |
| 7,422,586 B2 | 9/2008 | Morris et al. |
| 7,425,835 B2 | 9/2008 | Eisele |
| 7,465,302 B2 | 12/2008 | Odell et al. |
| 7,468,499 B2 | 12/2008 | Canini et al. |
| 7,470,272 B2 | 12/2008 | Mulier et al. |
| 7,477,080 B1 | 1/2009 | Fest |
| 7,479,140 B2 | 1/2009 | Ellman et al. |
| 7,491,199 B2 | 2/2009 | Goble |
| 7,491,201 B2 | 2/2009 | Shields et al. |
| 7,503,917 B2 | 3/2009 | Sartor et al. |
| 7,511,472 B1 | 3/2009 | Xia et al. |
| 7,513,896 B2 | 4/2009 | Orszulak |
| 7,517,351 B2 | 4/2009 | Culp et al. |
| 7,525,398 B2 | 4/2009 | Nishimura et al. |
| 7,568,619 B2 | 8/2009 | Todd et al. |
| 7,573,693 B2 | 8/2009 | Hornung |
| 7,582,084 B2 | 9/2009 | Swanson et al. |
| 7,621,041 B2 | 11/2009 | Banerji et al. |
| 7,628,786 B2 | 12/2009 | Plaven et al. |
| 7,648,499 B2 | 1/2010 | Orszulak et al. |
| 7,651,492 B2 | 1/2010 | Wham |
| 7,651,493 B2 | 1/2010 | Arts et al. |
| 7,655,003 B2 | 2/2010 | Lorang et al. |
| 7,666,182 B2 | 2/2010 | Klett et al. |
| 7,675,429 B2 | 3/2010 | Cernasov |
| 7,678,105 B2 | 3/2010 | McGreevy et al. |
| 7,722,601 B2 | 5/2010 | Wham et al. |
| 7,731,717 B2 | 6/2010 | Odom et al. |
| 7,736,358 B2 | 6/2010 | Shores et al. |
| 7,736,359 B2 | 6/2010 | McPherson |
| 7,744,593 B2 | 6/2010 | Mihori |
| 7,749,217 B2 | 7/2010 | Podhajsky |
| 7,766,693 B2 | 8/2010 | Sartor et al. |
| 7,766,905 B2 | 8/2010 | Paterson et al. |
| 7,780,662 B2 | 8/2010 | Bahney |
| 7,780,764 B2 | 8/2010 | Baksh |
| 7,794,457 B2 | 9/2010 | McPherson et al. |
| 7,799,020 B2 | 9/2010 | Shores et al. |
| 7,799,026 B2 | 9/2010 | Schechter et al. |
| 7,824,400 B2 | 11/2010 | Keppel |
| 7,834,484 B2 | 11/2010 | Sartor |
| 7,846,156 B2 | 12/2010 | Malis et al. |
| 7,863,841 B2 | 1/2011 | Menegoli et al. |
| 7,863,984 B1 | 1/2011 | Behnke |
| 7,864,129 B2 | 1/2011 | Konishi |
| 7,879,029 B2 | 2/2011 | Jimenez |
| 7,879,033 B2 | 2/2011 | Sartor et al. |
| 7,901,400 B2 | 3/2011 | Wham et al. |
| 7,927,328 B2 | 4/2011 | Orszulak et al. |
| 7,947,039 B2 | 5/2011 | Sartor |
| 7,956,620 B2 | 6/2011 | Gilbert |
| 7,959,626 B2 | 6/2011 | Hong et al. |
| 7,972,328 B2 | 7/2011 | Wham et al. |
| 7,972,332 B2 | 7/2011 | Arts et al. |
| 7,976,544 B2 | 7/2011 | McClurken et al. |
| 8,004,121 B2 | 8/2011 | Sartor |
| 8,012,150 B2 | 9/2011 | Wham et al. |
| 8,025,660 B2 | 9/2011 | Plaven et al. |
| 8,034,049 B2 | 10/2011 | Odom et al. |
| 8,038,676 B2 | 10/2011 | Fischer |
| 8,070,746 B2 | 12/2011 | Orton et al. |
| 8,080,008 B2 | 12/2011 | Wham et al. |
| 8,083,735 B2 | 12/2011 | Morris |
| 8,096,961 B2 | 1/2012 | Orszulak et al. |
| 8,104,596 B2 | 1/2012 | Kim et al. |
| 8,105,323 B2 | 1/2012 | Buysse et al. |
| 8,113,057 B2 | 2/2012 | Orszulak et al. |
| 8,133,218 B2 | 3/2012 | Daw et al. |
| 8,133,222 B2 | 3/2012 | Ormsby |
| 8,147,485 B2 | 4/2012 | Wham et al. |
| 8,152,800 B2 | 4/2012 | Behnke |
| 8,152,801 B2 | 4/2012 | Goldberg et al. |
| 8,152,802 B2 | 4/2012 | Podhajsky et al. |
| 8,162,932 B2 | 4/2012 | Podhajsky et al. |
| 8,167,875 B2 | 5/2012 | Podhajsky et al. |
| 8,174,267 B2 | 5/2012 | Brannan et al. |
| 8,187,262 B2 | 5/2012 | Orszulak |
| 8,200,317 B2 | 6/2012 | Baxi et al. |
| 8,202,271 B2 | 6/2012 | Orszulak |
| 8,211,100 B2 | 7/2012 | Podhajsky et al. |

(56) References Cited

U.S. PATENT DOCUMENTS

| | | |
|---|---|---|
| 8,216,219 B2 | 7/2012 | Desinger et al. |
| 8,216,220 B2 | 7/2012 | Jensen et al. |
| 8,216,223 B2 | 7/2012 | Wham et al. |
| 8,226,639 B2 | 7/2012 | Podhajsky et al. |
| 8,231,553 B2 | 7/2012 | Joseph et al. |
| 8,231,614 B2 | 7/2012 | Dunning et al. |
| 8,231,616 B2 | 7/2012 | McPherson et al. |
| 8,235,917 B2 | 8/2012 | Joseph et al. |
| 8,241,278 B2 | 8/2012 | Sartor |
| 8,242,782 B2 | 8/2012 | Brannan et al. |
| 8,248,075 B2 | 8/2012 | Brannan et al. |
| 8,257,349 B2 | 9/2012 | Orszulak |
| 8,257,350 B2 | 9/2012 | Marion |
| 8,262,652 B2 | 9/2012 | Podhajsky |
| 8,267,928 B2 | 9/2012 | Orszulak et al. |
| 8,267,929 B2 | 9/2012 | Wham et al. |
| 8,287,528 B2 | 10/2012 | Wham et al. |
| 8,287,529 B2 | 10/2012 | Orszulak |
| 8,292,883 B2 | 10/2012 | Kabaya et al. |
| 8,298,223 B2 | 10/2012 | Wham et al. |
| 8,303,337 B2 | 11/2012 | Ballard et al. |
| 8,303,580 B2 | 11/2012 | Wham et al. |
| 8,333,759 B2 | 12/2012 | Podhajsky |
| 8,346,370 B2 | 1/2013 | Haley et al. |
| 8,353,903 B2 | 1/2013 | Podhajsky |
| 8,353,905 B2 | 1/2013 | Jensen et al. |
| 8,377,053 B2 | 2/2013 | Orszulak |
| 8,377,054 B2 | 2/2013 | Gilbert |
| 8,382,751 B2 | 2/2013 | Gilbert et al. |
| 8,398,627 B2 | 3/2013 | Hosier |
| 8,403,924 B2 | 3/2013 | Behnke et al. |
| 8,409,186 B2 | 4/2013 | Behnke et al. |
| 8,454,590 B2 | 6/2013 | Smith |
| 8,460,284 B2 | 6/2013 | Aronow et al. |
| 8,469,956 B2 | 6/2013 | McKenna et al. |
| 8,475,447 B2 | 7/2013 | Orszulak et al. |
| 8,485,993 B2 | 7/2013 | Orszulak et al. |
| 8,486,061 B2 | 7/2013 | Podhajsky |
| 8,512,232 B2 | 8/2013 | Rothberg et al. |
| 8,523,855 B2 | 9/2013 | Keppel |
| 8,540,709 B2 | 9/2013 | Allen |
| 8,542,019 B2 | 9/2013 | Brannan et al. |
| 8,652,128 B2 | 2/2014 | Ward |
| 2001/0034519 A1 | 10/2001 | Goble et al. |
| 2002/0022836 A1 | 2/2002 | Goble et al. |
| 2002/0029036 A1 | 3/2002 | Goble et al. |
| 2003/0153908 A1 | 8/2003 | Goble et al. |
| 2003/0181898 A1* | 9/2003 | Bowers .............. A61B 18/1206 606/34 |
| 2003/0229344 A1 | 12/2003 | Dycus et al. |
| 2004/0015159 A1 | 1/2004 | Slater et al. |
| 2004/0030330 A1 | 2/2004 | Brassell et al. |
| 2004/0068304 A1 | 4/2004 | Paton et al. |
| 2004/0097912 A1 | 5/2004 | Gonnering |
| 2004/0097915 A1* | 5/2004 | Refior .............. A61B 18/1206 606/34 |
| 2004/0133189 A1 | 7/2004 | Sakurai |
| 2004/0172016 A1 | 9/2004 | Bek et al. |
| 2004/0193021 A1 | 9/2004 | Zdeblick et al. |
| 2005/0004634 A1 | 1/2005 | Ricart et al. |
| 2005/0021020 A1 | 1/2005 | Blaha |
| 2005/0109111 A1 | 5/2005 | Manlove et al. |
| 2005/0109935 A1 | 5/2005 | Manlove et al. |
| 2005/0113722 A1* | 5/2005 | Schultheiss ...... A61B 17/22004 601/4 |
| 2005/0131390 A1 | 6/2005 | Heinrich et al. |
| 2006/0079774 A1 | 4/2006 | Anderson |
| 2006/0111711 A1 | 5/2006 | Goble |
| 2006/0155270 A1 | 7/2006 | Hancock et al. |
| 2006/0161148 A1 | 7/2006 | Behnke |
| 2006/0191926 A1 | 8/2006 | Ray et al. |
| 2006/0224053 A1 | 10/2006 | Black et al. |
| 2006/0224152 A1 | 10/2006 | Behnke et al. |
| 2006/0229595 A1* | 10/2006 | Newton .............. A61B 18/1485 606/34 |
| 2006/0291178 A1 | 12/2006 | Shih |
| 2007/0088413 A1 | 4/2007 | Weber et al. |
| 2007/0093801 A1 | 4/2007 | Behnke |
| 2007/0173802 A1 | 7/2007 | Keppel |
| 2007/0173803 A1 | 7/2007 | Wham et al. |
| 2007/0173805 A1 | 7/2007 | Weinberg et al. |
| 2007/0173811 A1 | 7/2007 | Couture et al. |
| 2007/0173813 A1 | 7/2007 | Odom |
| 2007/0203481 A1 | 8/2007 | Gregg et al. |
| 2007/0265612 A1 | 11/2007 | Behnke et al. |
| 2007/0282320 A1 | 12/2007 | Buysse et al. |
| 2008/0004619 A1 | 1/2008 | Malis et al. |
| 2008/0015563 A1 | 1/2008 | Hoey et al. |
| 2008/0015570 A1 | 1/2008 | Ormsby et al. |
| 2008/0071257 A1 | 3/2008 | Kotmel et al. |
| 2008/0071260 A1 | 3/2008 | Shores |
| 2008/0132893 A1 | 6/2008 | D'Amelio et al. |
| 2008/0147056 A1 | 6/2008 | van der Weide et al. |
| 2008/0177199 A1 | 7/2008 | Podhajsky |
| 2008/0203997 A1 | 8/2008 | Foran et al. |
| 2008/0234574 A1 | 9/2008 | Hancock et al. |
| 2008/0262489 A1 | 10/2008 | Steinke |
| 2008/0281311 A1 | 11/2008 | Dunning et al. |
| 2008/0281315 A1 | 11/2008 | Gines |
| 2008/0281316 A1 | 11/2008 | Carlton et al. |
| 2008/0287943 A1 | 11/2008 | Weber et al. |
| 2008/0319350 A1 | 12/2008 | Wallace et al. |
| 2009/0018536 A1 | 1/2009 | Behnke |
| 2009/0030477 A1 | 1/2009 | Jarrard |
| 2009/0082765 A1 | 3/2009 | Collins et al. |
| 2009/0146635 A1 | 6/2009 | Qiu et al. |
| 2009/0157071 A1 | 6/2009 | Wham et al. |
| 2009/0234350 A1 | 9/2009 | Behnke et al. |
| 2009/0240244 A1 | 9/2009 | Malis et al. |
| 2009/0248003 A1 | 10/2009 | Orszulak |
| 2009/0248006 A1 | 10/2009 | Paulus et al. |
| 2009/0248007 A1 | 10/2009 | Falkenstein et al. |
| 2009/0254077 A1 | 10/2009 | Craig |
| 2009/0259224 A1 | 10/2009 | Wham et al. |
| 2009/0292283 A1 | 11/2009 | Odom |
| 2010/0030210 A1 | 2/2010 | Paulus |
| 2010/0042093 A9 | 2/2010 | Wham et al. |
| 2010/0057076 A1 | 3/2010 | Behnke et al. |
| 2010/0063494 A1 | 3/2010 | Orszulak |
| 2010/0063497 A1 | 3/2010 | Orszulak |
| 2010/0076424 A1 | 3/2010 | Carr |
| 2010/0082022 A1 | 4/2010 | Haley et al. |
| 2010/0082023 A1 | 4/2010 | Brannan et al. |
| 2010/0082083 A1 | 4/2010 | Brannan et al. |
| 2010/0082084 A1 | 4/2010 | Brannan et al. |
| 2010/0094271 A1 | 4/2010 | Ward et al. |
| 2010/0094275 A1 | 4/2010 | Wham |
| 2010/0094288 A1 | 4/2010 | Kerr |
| 2010/0114090 A1 | 5/2010 | Hosier |
| 2010/0137854 A1 | 6/2010 | Hosier |
| 2010/0168572 A1 | 7/2010 | Sliwa et al. |
| 2010/0168730 A1 | 7/2010 | Hancock et al. |
| 2010/0168741 A1 | 7/2010 | Sanai et al. |
| 2010/0179533 A1 | 7/2010 | Podhajsky |
| 2010/0191233 A1 | 7/2010 | Wham et al. |
| 2010/0211063 A1 | 8/2010 | Wham et al. |
| 2010/0217258 A1 | 8/2010 | Floume et al. |
| 2010/0217264 A1 | 8/2010 | Odom et al. |
| 2010/0268220 A1 | 10/2010 | Johnson et al. |
| 2010/0318080 A1 | 12/2010 | Keppel |
| 2011/0028963 A1 | 2/2011 | Gilbert |
| 2011/0054460 A1* | 3/2011 | Gilbert .............. A61B 18/1233 606/33 |
| 2011/0060329 A1 | 3/2011 | Gilbert et al. |
| 2011/0071516 A1 | 3/2011 | Gregg |
| 2011/0071521 A1 | 3/2011 | Gilbert |
| 2011/0077631 A1 | 3/2011 | Keller |
| 2011/0077639 A1 | 3/2011 | Brannan et al. |
| 2011/0087213 A1 | 4/2011 | Messerly et al. |
| 2011/0112530 A1 | 5/2011 | Keller |
| 2011/0115562 A1 | 5/2011 | Gilbert |
| 2011/0144635 A1 | 6/2011 | Harper et al. |
| 2011/0178516 A1 | 7/2011 | Orszulak et al. |
| 2011/0204903 A1 | 8/2011 | Gilbert |

(56) References Cited

U.S. PATENT DOCUMENTS

| | | |
|---|---|---|
| 2011/0208179 A1 | 8/2011 | Prakash et al. |
| 2011/0213354 A1 | 9/2011 | Smith |
| 2011/0213355 A1 | 9/2011 | Behnke, II |
| 2011/0224663 A1 | 9/2011 | Heim et al. |
| 2011/0301607 A1 | 12/2011 | Couture |
| 2011/0318948 A1 | 12/2011 | Plaven et al. |
| 2011/0319881 A1 | 12/2011 | Johnston |
| 2012/0004703 A1 | 1/2012 | Deborski et al. |
| 2012/0010610 A1 | 1/2012 | Keppel |
| 2012/0022521 A1 | 1/2012 | Odom et al. |
| 2012/0028373 A1 | 2/2012 | Belen et al. |
| 2012/0029515 A1 | 2/2012 | Couture |
| 2012/0089139 A1 | 4/2012 | Wham et al. |
| 2012/0101491 A1 | 4/2012 | Blaha |
| 2012/0116266 A1* | 5/2012 | Houser ............ A61B 17/00234 601/2 |
| 2012/0116268 A1 | 5/2012 | Orszulak et al. |
| 2012/0130256 A1 | 5/2012 | Buysse et al. |
| 2012/0150170 A1 | 6/2012 | Buysse et al. |
| 2012/0172866 A1 | 7/2012 | Behnke, II |
| 2012/0179156 A1 | 7/2012 | Behnke, II |
| 2012/0215216 A1* | 8/2012 | Friedrichs ......... A61B 18/1206 606/38 |
| 2012/0220997 A1 | 8/2012 | Johnston |
| 2012/0239020 A1 | 9/2012 | Cunningham |
| 2012/0239025 A1 | 9/2012 | Smith |
| 2012/0239026 A1 | 9/2012 | Orszulak et al. |
| 2012/0265194 A1 | 10/2012 | Podhajsky |
| 2012/0265195 A1 | 10/2012 | Gilbert |
| 2012/0303017 A1 | 11/2012 | Brannan et al. |
| 2012/0310241 A1 | 12/2012 | Orszulak |
| 2012/0316555 A1 | 12/2012 | Orszulak et al. |
| 2012/0316556 A1 | 12/2012 | Podhajsky |
| 2013/0006235 A1 | 1/2013 | Podhajsky et al. |
| 2013/0023867 A1 | 1/2013 | Collins |
| 2013/0023869 A1 | 1/2013 | Orszulak |
| 2013/0023870 A1 | 1/2013 | Collins |
| 2013/0023871 A1 | 1/2013 | Collins |
| 2013/0035679 A1 | 2/2013 | Orszulak |
| 2013/0041364 A1 | 2/2013 | Orszulak |
| 2013/0041367 A1 | 2/2013 | Wham et al. |
| 2013/0053840 A1 | 2/2013 | Krapohl et al. |
| 2013/0066311 A1 | 3/2013 | Smith et al. |
| 2013/0067725 A1 | 3/2013 | Behnke, II et al. |
| 2013/0072920 A1 | 3/2013 | Behnke, II et al. |
| 2013/0072921 A1 | 3/2013 | Behnke, II et al. |
| 2013/0072922 A1 | 3/2013 | Behnke, II et al. |
| 2013/0072923 A1 | 3/2013 | Behnke, II et al. |
| 2013/0079763 A1 | 3/2013 | Heckel et al. |
| 2013/0103023 A1 | 4/2013 | Monson et al. |
| 2013/0158541 A1 | 6/2013 | Orszulak |
| 2013/0178848 A1 | 7/2013 | Gilbert et al. |
| 2013/0184698 A1 | 7/2013 | Behnke, II et al. |
| 2013/0184699 A1 | 7/2013 | Behnke, II et al. |
| 2013/0190750 A1 | 7/2013 | Behnke, II et al. |
| 2013/0190751 A1 | 7/2013 | Brannan |
| 2013/0193952 A1 | 8/2013 | Krapohl |
| 2013/0197510 A1 | 8/2013 | Heckel |
| 2013/0197874 A1 | 8/2013 | Heckel |
| 2013/0215216 A1 | 8/2013 | Li et al. |
| 2013/0249721 A1 | 9/2013 | Smith |
| 2013/0253501 A1 | 9/2013 | Joseph |
| 2013/0261616 A1 | 10/2013 | Prakash et al. |
| 2013/0267944 A1 | 10/2013 | Krapohl |
| 2013/0274729 A1 | 10/2013 | Orszulak |
| 2013/0304049 A1 | 11/2013 | Behnke, II et al. |
| 2013/0345696 A1 | 12/2013 | Behnke, II et al. |
| 2014/0002056 A1 | 1/2014 | Moul et al. |
| 2014/0015535 A1 | 1/2014 | Lopez |

FOREIGN PATENT DOCUMENTS

| | | |
|---|---|---|
| DE | 390937 C | 3/1924 |
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 10 2008058737 A1 | 4/2010 |
| EP | 0 246 350 A1 | 11/1987 |
| EP | 267403 A2 | 5/1988 |
| EP | 296777 A2 | 12/1988 |
| EP | 0309942 A2 | 4/1989 |
| EP | 310431 A2 | 4/1989 |
| EP | 325456 A2 | 7/1989 |
| EP | 336742 A2 | 10/1989 |
| EP | 390937 A1 | 10/1990 |
| EP | 0503200 A2 | 9/1992 |
| EP | 0 556 705 A1 | 8/1993 |
| EP | 569130 A1 | 11/1993 |
| EP | 608609 A2 | 8/1994 |
| EP | 617925 A1 | 10/1994 |
| EP | 694291 A1 | 1/1996 |
| EP | 0 836 868 A2 | 4/1998 |
| EP | 870473 A2 | 10/1998 |
| EP | 0878169 A1 | 11/1998 |
| EP | 880220 A2 | 11/1998 |
| EP | 0 882 955 A1 | 12/1998 |
| EP | 0640317 B1 | 9/1999 |
| EP | 1051948 A2 | 11/2000 |
| EP | 1053720 | 11/2000 |
| EP | 1146827 A1 | 10/2001 |
| EP | 1151725 A1 | 11/2001 |
| EP | 1157667 A2 | 11/2001 |
| EP | 1263181 A1 | 12/2002 |
| EP | 1278007 | 1/2003 |
| EP | 1293171 A2 | 3/2003 |
| EP | 1366724 A1 | 12/2003 |
| EP | 1472984 | 11/2004 |
| EP | 1495712 A1 | 1/2005 |
| EP | 1500378 A1 | 1/2005 |
| EP | 1535581 | 6/2005 |
| EP | 1594392 A2 | 11/2005 |
| EP | 1609430 | 12/2005 |
| EP | 1645235 A1 | 4/2006 |
| EP | 1681026 A2 | 7/2006 |
| EP | 1707143 | 10/2006 |
| EP | 1707144 A1 | 10/2006 |
| EP | 1744354 A2 | 1/2007 |
| EP | 1776929 A1 | 4/2007 |
| EP | 1810628 | 7/2007 |
| EP | 1810630 A1 | 7/2007 |
| EP | 1810631 A2 | 7/2007 |
| EP | 1810632 A1 | 7/2007 |
| EP | 1810633 A2 | 7/2007 |
| EP | 1810634 A1 | 7/2007 |
| EP | 1849425 A1 | 10/2007 |
| EP | 1854423 A2 | 11/2007 |
| EP | 1862137 A1 | 12/2007 |
| EP | 1902681 A1 | 3/2008 |
| EP | 1994904 | 11/2008 |
| EP | 2025297 A2 | 2/2009 |

(56) References Cited

FOREIGN PATENT DOCUMENTS

| | | |
|---|---|---|
| EP | 2042116 A1 | 4/2009 |
| EP | 2100566 A1 | 9/2009 |
| EP | 2111812 A2 | 10/2009 |
| EP | 2156800 A1 | 2/2010 |
| EP | 2253286 A1 | 11/2010 |
| EP | 2301463 A1 | 3/2011 |
| EP | 2345454 A1 | 7/2011 |
| EP | 2469699 A2 | 6/2012 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| GB | 607850 A | 9/1948 |
| GB | 702510 A | 1/1954 |
| GB | 855459 A | 11/1960 |
| GB | 902775 A | 8/1962 |
| GB | 1290304 A | 9/1972 |
| GB | 2154881 A | 9/1985 |
| GB | 2164473 A | 3/1986 |
| GB | 2214430 A | 9/1989 |
| GB | 2331247 A | 5/1999 |
| GB | 2358934 A | 8/2001 |
| GB | 2434872 A | 8/2007 |
| JP | 63 005876 A | 1/1988 |
| JP | 2002-065690 A | 3/2002 |
| JP | 2005-185657 A | 7/2005 |
| SU | 166452 | 11/1964 |
| SU | 727201 A2 | 4/1980 |
| WO | 92/06642 | 4/1992 |
| WO | 92/07622 A1 | 5/1992 |
| WO | 93/20747 A1 | 10/1993 |
| WO | 93/24066 A1 | 12/1993 |
| WO | 94/10922 A1 | 5/1994 |
| WO | 94/24949 A1 | 11/1994 |
| WO | 94/28809 A1 | 12/1994 |
| WO | 95/09577 A1 | 4/1995 |
| WO | 95/18575 A1 | 7/1995 |
| WO | 95/19148 A1 | 7/1995 |
| WO | 95/25471 A2 | 9/1995 |
| WO | 95/25472 A1 | 9/1995 |
| WO | 96/02180 A2 | 2/1996 |
| WO | 96/04860 A1 | 2/1996 |
| WO | 96/08794 A1 | 3/1996 |
| WO | 96/18349 A2 | 6/1996 |
| WO | 96/29946 A1 | 10/1996 |
| WO | 96/39085 A1 | 12/1996 |
| WO | 96/39086 A1 | 12/1996 |
| WO | 96/39088 A1 | 12/1996 |
| WO | 96/39914 A1 | 12/1996 |
| WO | 97/06739 A2 | 2/1997 |
| WO | 97/06740 A2 | 2/1997 |
| WO | 97/06855 A2 | 2/1997 |
| WO | 97/10763 A1 | 3/1997 |
| WO | 97/11648 A2 | 4/1997 |
| WO | 97/17029 A1 | 5/1997 |
| WO | 97/43971 A2 | 11/1997 |
| WO | 98/07378 A1 | 2/1998 |
| WO | 98/18395 A1 | 5/1998 |
| WO | 98/27880 | 7/1998 |
| WO | 99/12607 A1 | 3/1999 |
| WO | 99/56647 A1 | 11/1999 |
| WO | 00/48672 A1 | 8/2000 |
| WO | 00/54683 A1 | 9/2000 |
| WO | 01/01847 | 1/2001 |
| WO | 02/00129 | 1/2002 |
| WO | 02/011634 | 2/2002 |
| WO | 02/032333 | 4/2002 |
| WO | 02/032335 | 4/2002 |
| WO | 02/045589 | 6/2002 |
| WO | 02/047565 | 6/2002 |
| WO | 02/053048 A1 | 7/2002 |
| WO | 02/088128 A1 | 11/2002 |
| WO | 03/047446 A1 | 6/2003 |
| WO | 03/090635 A1 | 11/2003 |
| WO | 03/092520 A1 | 11/2003 |
| WO | 03/090630 A3 | 4/2004 |
| WO | 04/028385 A1 | 4/2004 |
| WO | 04/043240 A2 | 5/2004 |
| WO | 04/047659 A2 | 6/2004 |
| WO | 04/052182 A2 | 6/2004 |
| WO | 04/073488 | 9/2004 |
| WO | 04/098385 A2 | 11/2004 |
| WO | 2004/098385 A2 | 11/2004 |
| WO | 04/103156 | 12/2004 |
| WO | 05/046496 A1 | 5/2005 |
| WO | 05/048809 | 6/2005 |
| WO | 05/050151 | 6/2005 |
| WO | 05/060365 A2 | 7/2005 |
| WO | 05/060849 A1 | 7/2005 |
| WO | 05/115235 A1 | 12/2005 |
| WO | 05/117735 A1 | 12/2005 |
| WO | 06/050888 A1 | 5/2006 |
| WO | 2006/059067 A1 | 6/2006 |
| WO | 06/105121 A2 | 10/2006 |
| WO | 07/055491 A1 | 5/2007 |
| WO | 07/067522 A2 | 6/2007 |
| WO | 2007/076924 A2 | 7/2007 |
| WO | 07/105963 A1 | 9/2007 |
| WO | 08/002517 A1 | 1/2008 |
| WO | 08/003058 A2 | 1/2008 |
| WO | 08/011575 A1 | 1/2008 |
| WO | 08/043999 A2 | 4/2008 |
| WO | 08/044000 A1 | 4/2008 |
| WO | 08/044013 A2 | 4/2008 |
| WO | 08/053532 A1 | 5/2008 |
| WO | 08/070562 A1 | 6/2008 |
| WO | 08/071914 A2 | 6/2008 |
| WO | 08/101356 A1 | 8/2008 |
| WO | 08/110756 A2 | 9/2008 |
| WO | 2010/129348 A1 | 11/2010 |

OTHER PUBLICATIONS

European Search Report issued in corresponding EP Application No. 14178300.1 dated Dec. 12, 2014.
Extended European Search Report for EP 14 18 4738 dated Apr. 10, 2015.
Wald et al., "Accidental Burns", JAMA, Aug. 16, 1971, vol. 217, No. 7, pp. 916-921.
Vallfors et al., "Automatically Controlled Bipolar Electrosoagulation—'COA-COMP'", Neurosurgical Review 7:2-3 (1984) pp. 187-190.
Sugita et al., "Bipolar Coagulator with Automatic Thermocontrol", J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487, Electronics World; Reed Business Publishing, Sutton, Surrey, BG vol. 99, No. 9. 1687.
Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator", 3 pp. Jan. 1989.

(56) References Cited

OTHER PUBLICATIONS

Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al., "The Measurement of Physiologic Events by Electrical Impedence", Am. J. MI, Jan. Mar. 1964, pp. 16-27.
Cosman et al., "Methods of Making Nervous System Lesions", In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance", Applied Neurophysiology 51: (1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . ", Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System" 2 pp. Nov. 1995.
U.S. Appl. No. 10/406,690 dated Apr. 3, 2003 inventor: Behnke.
U.S. Appl. No. 10/573,713 dated Mar. 28, 2006 inventor: Wham.
U.S. Appl. No. 10/761,524 dated Jan. 21, 2004 inventor: Wham.
U.S. Appl. No. 11/242,458 dated Oct. 3, 2005 inventor: Becker.
U.S. Appl. No. 13/943,518 dated Jul. 16, 2013 inventor: Orszulak et al.
U.S. Appl. No. 14/069,534 dated Nov. 1, 2013 inventor: Digmann.
U.S. Appl. No. 14/096,341 dated Dec. 4, 2013 inventor: Johnson.
U.S. Appl. No. 14/098,859 dated Dec. 6, 2013 inventor: Johnson.
U.S. Appl. No. 14/100,113 dated Dec. 9, 2013 inventor: Gilbert.
U.S. Appl. No. 14/147,294 dated Jan. 3, 2014 inventor: Gilbert.
U.S. Appl. No. 14/147,312 dated Jan. 3, 2014 inventor: Gilbert.
U.S. Appl. No. 14/174,551 dated Feb. 6, 2014 inventor: Johnson.
U.S. Appl. No. 14/174,607 dated Feb. 6, 2014 inventor: Friedrichs.
U.S. Appl. No. 14/179,724 dated Feb. 13, 2014 inventor: Johnson.
U.S. Appl. No. 14/180,965 dated Feb. 14, 2014 inventor: Larson.
U.S. Appl. No. 14/181,114 dated Feb. 14, 2014 inventor: Larson.
U.S. Appl. No. 14/182,797 dated Feb. 18, 2014 inventor: Wham.
U.S. Appl. No. 14/183,196 dated Feb. 18, 2014 inventor: Krapohl.
U.S. Appl. No. 14/190,830 dated Feb. 26, 2014 inventor: Johnson.
U.S. Appl. No. 14/190,895 dated Feb. 26, 2014 inventor: Gilbert.
U.S. Appl. No. 14/192,112 dated Feb. 27, 2014 inventor: Weinberg.
U.S. Appl. No. 14/255,051 dated Apr. 17, 2014 inventor: Coulson.
Chinese Office Action dated Sep. 28, 2017 in corresponding Chinese Patent Application No. 201410355883.8 together with English translation, 17 pages.

* cited by examiner

SYSTEMS AND METHODS FOR GENERATING ELECTROSURGICAL ENERGY USING A MULTISTAGE POWER CONVERTER

CROSS REFERENCE TO RELATED APPLICATION

The present application claims the benefit of and priority to U.S. Provisional Application No. 61/858,037, filed on Jul. 24, 2013, the entire contents of which are incorporated herein by reference.

BACKGROUND

1. Technical Field

The present disclosure relates to electrosurgery. More particularly, the present disclosure relates to electrosurgical generators and methods that use a multi-stage power converter for generating electrosurgical energy.

2. Background of Related Art

Electrosurgery involves the application of high-frequency electric current to cut or modify biological tissue during an electrosurgical procedure. Electrosurgery is performed using an electrosurgical generator, an active electrode, and a return electrode. The electrosurgical generator (also referred to as a power supply or waveform generator) generates an alternating current (AC), which is applied to a patient's tissue through the active electrode and is returned to the electrosurgical generator through the return electrode. The alternating current typically has a frequency above 100 kilohertz (kHz) to avoid muscle and/or nerve stimulation.

During electrosurgery, the AC generated by the electrosurgical generator is conducted through tissue disposed between the active and return electrodes. The tissue's impedance converts the electrical energy (also referred to as electrosurgical energy) associated with the AC into heat, which causes the tissue temperature to rise. The electrosurgical generator controls the heating of the tissue by controlling the electric power (i.e., electrical energy per time) provided to the tissue. Although many other variables affect the total heating of the tissue, increased current density usually leads to increased heating. The electrosurgical energy is typically used for cutting, dissecting, ablating, coagulating, and/or sealing tissue.

The two basic types of electrosurgery employed are monopolar and bipolar electrosurgery. Both of these types of electrosurgery use an active electrode and a return electrode. In bipolar electrosurgery, the surgical instrument includes an active electrode and a return electrode on the same instrument or in very close proximity to one another, which cause current to flow through a small amount of tissue. In monopolar electrosurgery, the return electrode is located elsewhere on the patient's body and is typically not a part of the electrosurgical instrument itself. In monopolar electrosurgery, the return electrode is part of a device typically referred to as a return pad.

As shown in FIG. 4, the ideal output power characteristic of an electrosurgical (ES) generator is constant current 410, followed by constant power 420, which is, in turn, followed by constant voltage 430 as a function of the increasing output impedance. To achieve this output power characteristic, the ES generator executes a control loop that samples the output voltage and current, calculates power and/or impedance based on the sampled output voltage and current, feeds the calculated power and/or impedance through a digital compensator, and then adjusts a control signal (e.g., adjusts the pulse width or phase shift of the control signal) that controls the power stage. This control loop, however, may be relatively slow compared to the switching frequency of the power stage. Therefore, the power stage may under-deliver or over-deliver the desired power to the tissue until the control loop catches up with the power stage and the system reaches steady state. For this and other reasons, current ES generators may fall short of providing the ideal output power characteristic.

SUMMARY

The electrosurgical systems and methods of the present disclosure improve the dynamic response of the inverter during power control and reduce the power deviations due to changes in tissue impedances, which reduce thermal spreading in tissue for a given power. The electrosurgical systems and methods of the present disclosure employ a two-staged power converter that provides a desired power level based on the impedance of tissue being treated during an electrosurgical procedure. The two-staged power converter includes a boost converter and a phase-shifted pulse width modulation (PS-PWM) resonant inverter. The boost converter converts input direct current to a desired direct current and the PS-PWM resonant inverter inverts the desired direct current to a desired alternating current suitable for a given electrosurgical procedure.

The boost converter is controlled by control signals generated based on a current programmed mode or a voltage control mode and a current programmed mode. The PS-PWM resonant inverter is controlled by control signals having a desired fixed phase. The control signals that are used to control the boost converter and the PS-PWM resonant inverter are determined based on the output characteristic, e.g., based on whether the output characteristic is constant current, constant power, or constant voltage.

In one aspect, the present disclosure features an electrosurgical generator that includes an power converter, a plurality of sensors, and a controller. The power converter is coupled to an electrical energy source and generates electrosurgical energy. The power converter includes a boost converter that converts a first direct current from the electrical energy source to a second direct current and a phase-shifted pulse width modulation (PS-PWM) resonant inverter that inverts the second direct current to an alternating current. The plurality of sensors sense voltage and current waveforms of the generated electrosurgical energy. The controller is coupled to the power converter and the plurality of sensors, and includes a signal processor and an output controller. The signal processor determines tissue impedance based on the voltage and current waveforms. The output controller selects one among a plurality of output characteristics based on the determined tissue impedance and generates a first control signal to control the boost converter and a second control signal to control the PS-PWM resonant inverter, according to the selected output characteristic.

The plurality of output characteristics may include a constant current output characteristic, a constant power output characteristic, and a constant voltage output characteristic. The output controller may shift from the constant current output characteristic to the constant power output characteristic and from the constant power output characteristic the constant voltage output characteristic based on the tissue impedance. The output controller may select the constant current output characteristic if the tissue impedance is less than a first predetermined value, the output controller may select the constant power output characteristic if the tissue impedance is greater than or equal to the first predetermined value and less than a second predetermined value, the output controller may select the constant voltage output characteristic if the tissue impedance is greater than or equal to the second predetermined value and less than a third predetermined value, and the first predetermined value may be less than the second predetermined value and the second predetermined value may be less than the third predetermined value.

When the output characteristic is a constant voltage output characteristic, the output controller may generate the first control signal under a voltage control mode and may generate the second control signal having a fixed phase. When the output characteristic is a constant current output characteristic, the output controller may generate the first control signal under a voltage control mode and may generate the second control signal having a fixed phase. When the output characteristic is a constant power output characteristic, the output controller may generate the first control signal under a current programmed mode and may generate the second control signal having a fixed phase. Alternatively, when the output characteristic is any one of a constant voltage output characteristic, a constant current output characteristic, and a constant power output characteristic, the output controller may generate the first control signal under a current programmed mode and may generate the second control signal having a fixed phase.

The output controller may operate the boost converter at a faster switching frequency than a switching frequency of the PS-PWM resonant inverter. The boost converter may include a plurality of boost converters to lower ripples of the voltage and current input to the PS-PWM resonant inverter.

The electrosurgical generator may further include analog-to-digital converters (ADCs) that sample the sensed voltage and current waveforms to obtain a predetermined number of samples of the sensed voltage and current waveforms. The predetermined number of samples may correspond to an integer multiple of an RF frequency of the sensed voltage and current waveforms. The signal processor may include a plurality of ADC controllers that provide control parameters to the ADCs. The control parameters may include a sampling frequency of the ADCs.

The plurality of sensors may include a Rogowski coil. The controller of the electrosurgical generator may be implemented by a field programmable gate array, an application specific integrated circuit, a digital signal processor, or a programmable digital signal processor.

The present disclosure, in another aspect, features a method for controlling an electrosurgical generator. The method includes converting a first direct current from an electrical energy source to a second direct current using a boost converter, converting the second direct current to an alternating current using a PS-PWM inverter, sensing a current of the boost converter and a voltage at an output of the PS-PWM inverter, determining an impedance of tissue being treated based on the sensed voltage and current waveforms, selecting a output characteristic based on the determined tissue impedance, and generating a first control signal to control the boost converter and a second control signal to control the PS-PWM inverter, according to a predetermined control mode for the selected output characteristic. The plurality of output characteristics may include a constant current output characteristic, a constant voltage output characteristic, and a constant power output characteristic.

When the output characteristic is a constant voltage output characteristic, the first control signal may be generated under a voltage control mode and the second control signal may be generated to have a fixed phase. When the output characteristic is a constant current output characteristic, the first control signal may be generated under a voltage control mode and the second control signal may be generated to have a fixed phase. When the output characteristic is a constant power output characteristic, the first control signal may be generated under a current programmed mode and the second control signal may be generated to have a fixed phase. Alternatively, when the output characteristic is any one of a constant voltage output characteristic, a constant current output characteristic, and a constant power output characteristic, the first control signal may be generated under a current programmed mode and the second control signal may be generated to have a fixed phase.

BRIEF DESCRIPTION OF THE DRWAINGS

Various embodiment of the present disclosure are described with reference to the accompanying drawings wherein.

DETAILED DESCRIPTION

To select an output characteristic among the constant current, constant voltage, and constant power output characteristics, typical methods sample output voltage and current waveforms, calculate power and/or impedance, feed these calculation results through a digital compensator, and then adjust the control variables of the output power converter's buck converter and resonant inverter. These processes are relatively slow compared to the switching frequency of the output power converter and, therefore, over-deliver or under-deliver the desired power until the control processes of the output power converter catch up and the system reaches a steady state. Thus, it is desirable to switch among the constant current, the constant power, and the constant voltage output characteristics quickly.

The systems and methods according to the present disclosure employ a multi-stage output power converter that can achieve a near ideal constant-current, constant-power, and constant-voltage output characteristic by changing the control methodology of each stage. The multi-stage output power converter may be a dual-stage output power converter that includes a buck/boost converter and a resonant inverter that are separately controlled according to selected control modes. The control modes are selected based on the desired output characteristic, that is, constant current, constant voltage, or constant power. The desired output characteristic, in turn, is selected based on the measured tissue impedance. In this manner, the systems and methods of the present disclosure provide a desired amount of power and switch between output characteristics more quickly.

The control methods according to the present disclosure may be implemented in hardware and firmware. Because of the improved control loop bandwidth that is achieved by the hardware according to the present disclosure, the firmware control may be simplified and updated at a slower rate than the resonant inverter output frequency.

Figure 1:
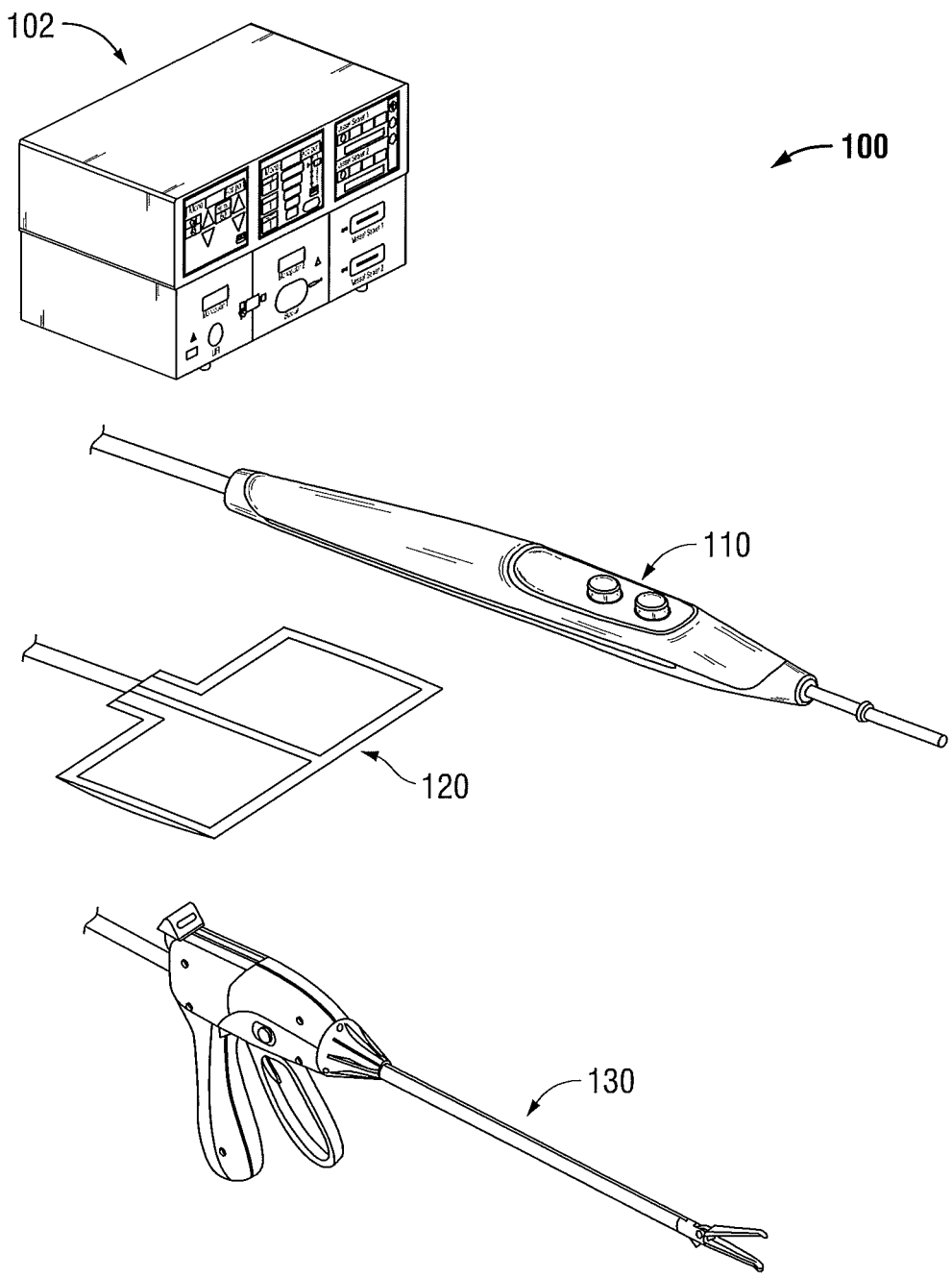
FIG. 1 is an illustration of an electrosurgical system in accordance with embodiments of the present disclosure.

FIG. 1 illustrates an electrosurgical system 100 in accordance with embodiments of the present disclosure. The electrosurgical system 100 includes an electrosurgical generator 102 which generates electrosurgical energy to treat tissue of a patient. The electrosurgical generator 102 generates an appropriate level of electrosurgical energy based on the selected mode of operation (e.g., cutting, coagulating, ablating, or sealing) and/or the sensed voltage and current waveforms of the generated electrosurgical energy. The electrosurgical system 100 may also include a plurality of output connectors corresponding to a variety of electrosurgical instruments.

The electrosurgical system 100 further includes a monopolar electrosurgical instrument 110 having an electrode for treating tissue of the patient (e.g., an electrosurgical cutting probe or ablation electrode) with a return pad 120. The monopolar electrosurgical instrument 110 can be connected to the electrosurgical generator 102 via one of the plurality of output connectors. The electrosurgical generator 102 may generate electrosurgical energy in the form of radio frequency (RF) energy. The electrosurgical energy is supplied to the monopolar electrosurgical instrument 110, which applies the electrosurgical energy to tissue. The electrosurgical energy is returned to the electrosurgical generator 102 through the return pad 120. The return pad 120 provides sufficient contact area with the patient's tissue so as to minimize the risk of tissue damage due to the electrosurgical energy applied to the tissue.

The electrosurgical system 100 also includes a bipolar electrosurgical instrument 130. The bipolar electrosurgical instrument 130 can be connected to the electrosurgical generator 102 via one of the plurality of output connectors. Alternating current is supplied to one of the two forceps, is applied to tissue, and is returned to the electrosurgical generator 102 through the other forceps.

The electrosurgical generator 102 may be any suitable type of generator and may include a plurality of connectors to accommodate various types of electrosurgical instruments (e.g., monopolar electrosurgical instrument 110 and bipolar electrosurgical instrument 130). The electrosurgical generator 102 may also be configured to operate in a variety of modes, such as ablation, cutting, coagulation, and sealing. The electrosurgical generator 102 may include a switching mechanism (e.g., relays) to switch the supply of RF energy among the connectors to which various electrosurgical instruments may be connected. For example, when an electrosurgical instrument 110 is connected to the electrosurgical generator 102, the switching mechanism switches the supply of RF energy to the monopolar plug. In embodiments, the electrosurgical generator 102 may be configured to provide RF energy to a plurality of instruments simultaneously.

The electrosurgical generator 102 includes a user interface having suitable user controls (e.g., buttons, activators, switches, or touch screens) for providing control parameters to the electrosurgical generator 102. These controls allow the user to adjust parameters of the electrosurgical energy (e.g., the power level or the shape of the output waveform) so that the electrosurgical energy is suitable for a particular surgical procedure (e.g., coagulating, ablating, tissue sealing, or cutting). The electrosurgical instruments 110 and 130 may also include a plurality of user controls. In addition, the electrosurgical generator 102 may include one or more display screens for displaying a variety of information related to the operation of the electrosurgical generator 102 (e.g., intensity settings and treatment complete indicators).

Figure 2:
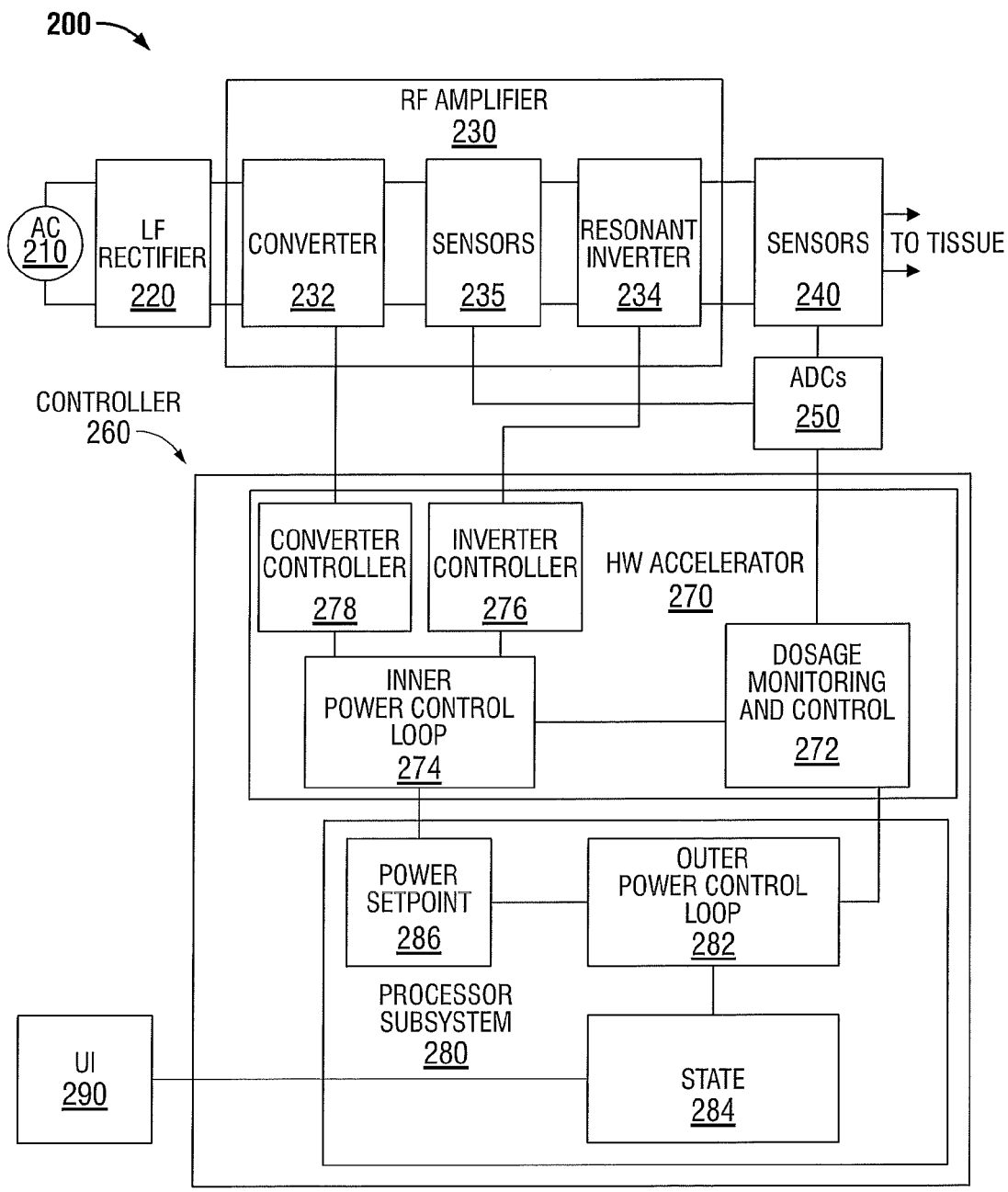
FIG. 2 is a circuit block diagram illustrating the generator circuitry of the electrosurgical generator of FIG. 1.

FIG. 2 is a circuit block diagram of generator circuitry 200 within the electrosurgical generator 102 of FIG. 1. The generator circuitry 200 includes a low frequency (LF) rectifier 220, a radio frequency (RF) amplifier 230, a plurality of sensors 235 and 240, analog-to-digital converters (ADCs) 250, a controller 260, which includes a hardware accelerator 270 and a processor subsystem 280, and a user interface (UI) 290. The generator circuitry 200 is configured to connect to an alternating current (AC) power source 210, such as a wall power outlet or other power outlet, which generates AC having a low frequency (e.g., 25 Hz, 50 Hz, or 60 Hz). The AC power source 210 provides AC power to the LF rectifier 220, which converts the AC to direct current (DC).

The direct current (DC) output from the LF rectifier 220 is provided to the RF amplifier 230, which includes a converter 232 and a resonant inverter 234. The combination of the converter 232 and the resonant inverter 234 forms a multi-stage power converter described in more detailed below. The converter 232 steps up or steps down the DC to a desired level. The resonant inverter 234 inverts the DC to an AC waveform to treat tissue. The AC waveform has a frequency suitable for an electrosurgical procedure (e.g., 472 kHz, 29.5 kHz, and 19.7 kHz).

The appropriate frequency for the electrosurgical energy may differ based on the electrosurgical procedures and modes of electrosurgery. For example, nerve and muscle stimulations cease at about 100,000 cycles per second (100 kHz) and some electrosurgical procedures can be performed safely at a radio frequency (RF) above 100 kHz. At frequencies over 100 kHz, the electrosurgical energy can pass through a patient to targeted tissue with minimal neuromuscular stimulation. For example, ablation uses a frequency of 472 kHz. Other electrosurgical procedures can be performed at frequencies lower than 100 kHz, e.g., 29.5 kHz or 19.7 kHz, with minimal risk of damaging nerves and muscles. The resonant inverter 234 may output AC signals with various frequencies suitable for electrosurgical operations.

As described above, the RF amplifier 230 includes a resonant inverter 234 which is coupled to the converter 232. The resonant inverter 234 matches the impedance at converter 232 to the impedance of the tissue so that there is maximum or optimal power transfer from the RF amplifier 230 to the tissue being treated.

The electrosurgical energy provided by the converter 232 of the RF amplifier 230 is controlled by the controller 260. The voltage and current waveforms of the electrosurgical energy output from the converter 232 and the resonant inverter 234 are sensed by the plurality of sensors 235, 240 and are provided to the controller 260, which generates control signals to control the output voltage and current waveforms of the converter 232 and the resonant inverter 234. The controller 260 also receives input commands from a user via the user interface (UI) 290. The UI 290 allows a user to select a type of electrosurgical procedure (e.g., monopolar or bipolar) and a mode (e.g., coagulation, ablation, sealing, or cutting), or input desired control parameters for the electrosurgical procedure or the mode. The UI 290 also includes a display (e.g., an LCD display) that displays, among other things, information related to characteristics of the electrosurgical energy (e.g., a selected power level).

The plurality of sensors 235, 240 may include two or more pairs or sets of voltage and current sensors that provide redundant measurements of the voltage and current waveforms. This redundancy ensures the reliability, accuracy, and stability of the voltage and current measurements at the output of the converter 232 and resonant inverter 234. In embodiments, the plurality of sensors 235, 240 may include fewer or more sets of voltage and current sensors depending on the application or the design requirements.

In embodiments, the current passing through the converter 232 is sensed by a current sensor of the plurality of sensors 235 and a voltage of the resonant inverter 234 is sensed by a voltage sensor of the plurality of sensors 240. The plurality of sensors 235, 240 may employ any known technology for measuring voltage and current including, for example, a Rogowski coil.

The sensed voltage and current waveforms are fed to analog-to-digital converters (ADCs) 250, which sample the sensed voltage and current waveforms to obtain digital samples of the voltage and current waveforms. The digital samples of the voltage and current waveforms are processed by the controller 260 and used to generate control signals to control the converter 232 and the resonant inverter 234 of the RF amplifier 230. The ADCs 250 may be configured to sample the sensed voltage and current waveforms at a sample period that is an integer multiple of the RF frequency of the voltage and current waveforms.

As shown in FIG. 2, the controller 260 includes a hardware accelerator 270 and a processor subsystem 280. The hardware accelerator 270 processes the output from the ADCs 250 and cooperates with the processor subsystem 280 to generate control signals for the converter 232 and resonant inverter 234 of the RF amplifier 230.

The hardware accelerator 270 includes a dosage monitoring and control (DMAC) 272, an inner power control loop 274, an inverter controller 276, and a converter controller 278. All or a portion of the controller 260 may be implemented by a field programmable gate array (FPGA), an application specific integrated circuit (ASIC), a digital signal processor (DSP), and/or a microcontroller.

The DMAC 272 receives samples of the voltage and current waveforms from the ADCs 250 and calculates the impedance of the tissue. The DMAC 272 then provides the impedance of the tissue to the inner power control loop 274, which generates control signals for the inverter controller 276 and the converter controller 278 based on the impedance of the tissue. The inverter controller 276, in turn, generates a first control signal to control the output of the resonant inverter 234 and the converter controller 278, in turn, generates a second control signal to control the output of the converter 232. The first and second control signals act to limit the RF amplifier's output voltage and current to a desired voltage and current as specified in a particular control mode. In this manner, the controller 260 controls the RF amplifier 230 to produce near deadbeat control of the output power.

The processor subsystem 280 includes an outer power control loop 282, a state machine 284, and a power setpoint circuit 286. The processor subsystem 280 generates a control signal based on the output of the DMAC 272 and parameters (e.g., electrosurgical mode) selected by the user via the UI 290. Specifically, the parameters selected by the user are provided to the state machine 284 which determines a state or mode of the generator circuitry 200. The outer power control loop 282 uses this state information and the output from the DMAC 272 to determine a control signal. The control signal is provided to the power setpoint circuit 286 which generates a power setpoint value based on the control signal.

The inner power control loop 274 uses the power setpoint value to generate appropriate control signals for controlling the converter 232 via the converter controller 278. If the user does not provide operational parameters to the state machine 284 via the UI 290, then the state machine 284 may maintain or enter a default state.

Figure 3:
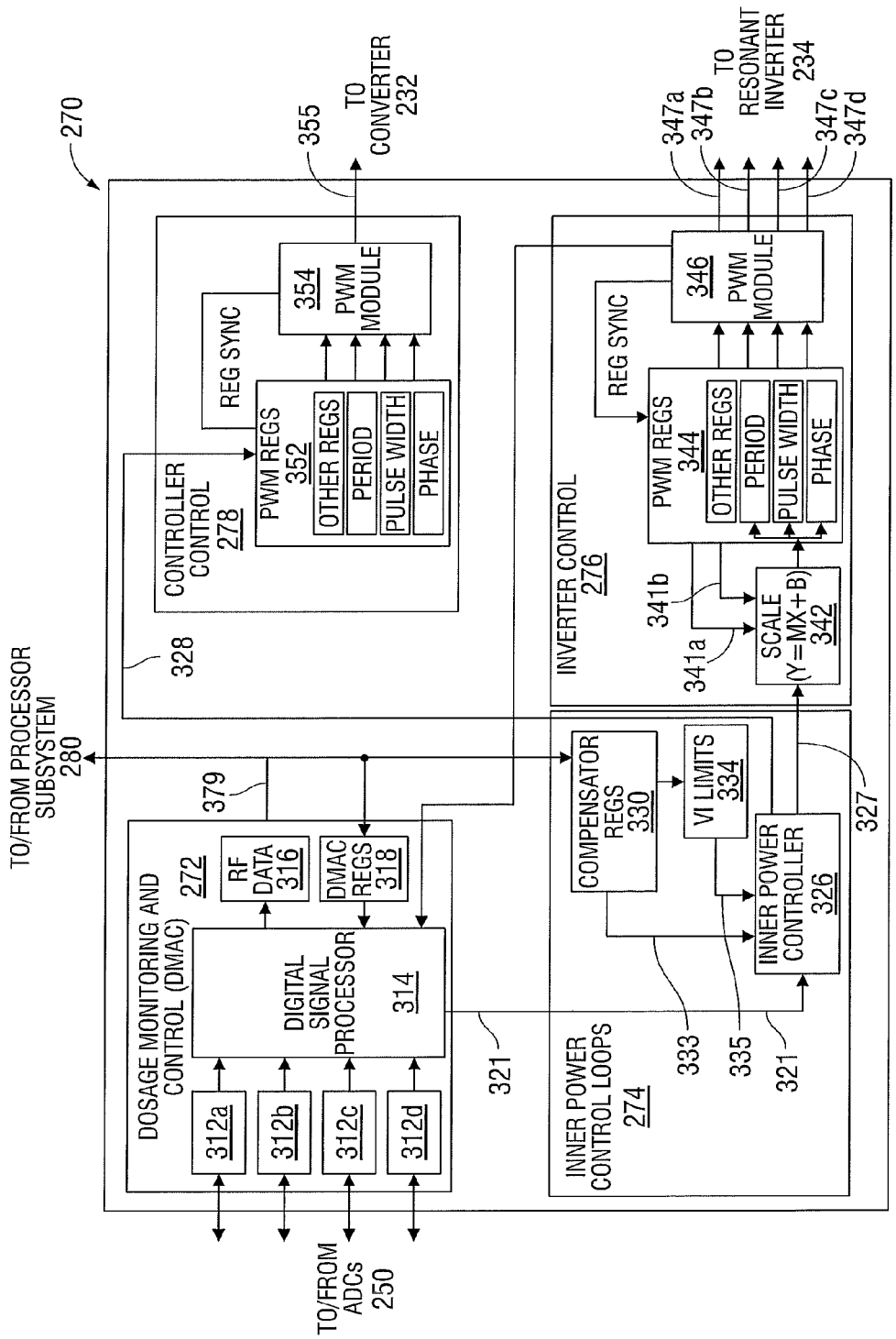
FIG. 3 is a circuit block diagram of a controller of the generator circuitry of FIG. 2.
Figure 4:
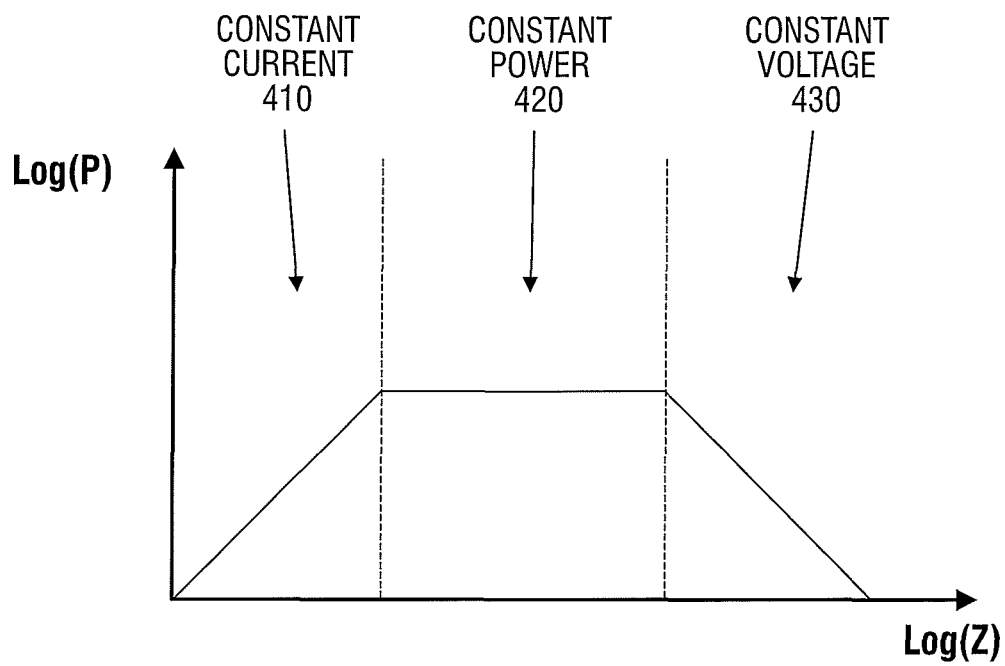
FIG. 4 is a graphical diagram of the ideal output characteristics of the electrosurgical generator of FIG. 1.

FIG. 3 is a circuit block diagram of the hardware accelerator 270 of FIG. 2. The hardware accelerator 270 implements functions of the generator circuitry 200 that may have special processing requirements such as high processing speeds. The hardware accelerator 270 includes the DMAC 272 and the inner power control loop 274 shown in FIG. 2.

The DMAC 272 includes four ADC controllers 312a-312d, a digital signal processor 314, RF data registers 316, and DMAC registers 318. The ADC controllers 312a-312d control the operation of the ADCs 250, which convert sensed voltage and current waveforms into digital data. The digital data is then provided to the digital signal processor 314 that implements various digital signal processing functions, some of which are described in more detail below.

The ADC controllers 312a-312d provide operational parameters, including a predetermined sampling rate, to the ADCs 250 so that the ADCs 250 sample the sensed voltage and current waveforms synchronously at a predetermined sampling rate, i.e., a predetermined number of samples per second, or a predetermined sampling period. The ADC controllers 312a-312d may be configured to control the ADCs 250 so that the sampling period corresponds to an integer multiple of the RF frequency of the voltage and current waveforms.

The DMAC 272 provides a control signal, which is the impedance of the tissue being treated, to the inner power control loop 274 via signal line 321 and to the processor subsystem 280 via signal line 379. The inner power control loop 274 processes the control signal and outputs a control signal to the inverter controller 276 and the converter controller 278. The inner power control loop 274 includes an inner power controller 326, compensator registers 330, and VI limiter 334.

When there is a user input, the processor subsystem 280 receives the user input and processes it with the outputs from the digital signal processor 314 via a signal line 379. The processor subsystem provides control signals via compensator registers 330 to a VI limiter 334, which corresponds to the power setpoint circuit 286 in FIG. 2. The VI limiter 334 then provides via signal line 335 a desired power profile (e.g., minimum and maximum limits on the power for a selected electrosurgical mode or operation) based on the user input and the output of the digital signal processor 314. The compensator registers 330 also provide via signal line 333 other control parameters to the inner power controller 326, which combines control parameters from the compensator registers 330, the VI limiter 334, and the impedance from the digital signal processor 314 to generate control signals and provide them to the inverter controller 276 via signal line 327 and to the converter controller 278 via signal line 328.

The inverter controller 276 receives a control parameter and outputs control signals that drive the resonant inverter 234. The inverter controller 276 includes a scale unit 342, PWM registers 344, and the PWM module 346. The scale unit 342 scales the output of the compensator registers 330 by multiplying and/or adding a scaling value to the output. The scale unit 342 receives a scaling value from the PWM registers 344 via signal lines 341a and 341b. The PWM registers 344 store several relevant parameters to control the resonant inverter 234, e.g., a period, a pulse width, and a phase of the AC signal to be generated by the resonant inverter 234 and other related parameters. The PWM module 346 receives outputs from the PWM registers 344 and generates four control signals 347a-347d that control four transistors of the resonant inverter 234 of the RF amplifier 230 of FIG. 2. The PWM module 346 also synchronizes its information with the information in the PWM registers 344 via a register sync signal.

The converter controller 278 receives a control signal and generates another control signal so that the converter 232 is controlled to amplify or step down direct current to a desired level suitable for the resonant inverter 234. The converter controller 278 includes PWM registers 352 and a PWM module 354. The PWM registers 352 receive outputs from the inner power control loop 274 and stores relevant parameters in the PWM registers 344 of the inverter controller 276. The PWM module 354 sends a register sync signal to the PWM registers 352 and generates a control signal 355 having a desired duty cycle to control the converter 232 of FIG. 2. Thus, the inner power control loop 274 controls the converter 232 and the resonant inverter 234 of the RF amplifier 230 based on processed sensor signals provided by the DMAC 272 and other signals provided to the hardware accelerator 270 via the processor subsystem 280.

Figure 5:
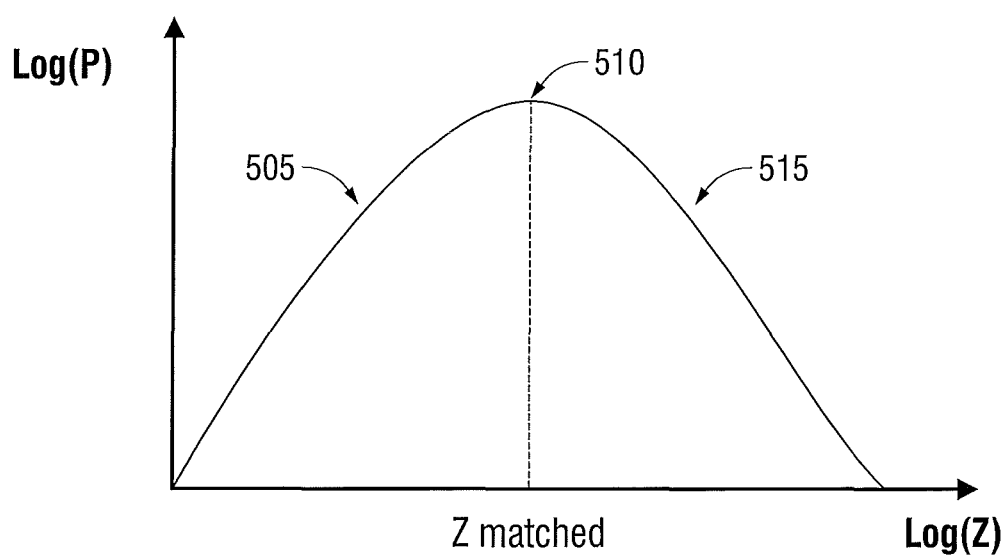
FIG. 5 is a graphical diagram of power transfer from the electrosurgical generator of FIG. 1 to tissue.

Current electrosurgical generators employ a variety of output power stages including a high-voltage DC (HVDC) power supply followed by a fixed PWM inverter, a HVDC power supply followed by a current source inverter, a phase-shifted PWM full bridge resonant inverter, a current-source parallel-resonant DC/AC inverter with a transformer, and an IGBT-based LCL-resonant inverter for high-frequency induction heating. These output power stages have an output impedance that affects the transfer of power to the load. As shown in FIG. 5, these output power stages exhibit an output power characteristic of the resonant inverter, in which the power initially increases along an asymptotic line 505 of constant current and then increases more slowly until the output impedance matches the source impedance of the electrosurgical generator. When the output impedance matches the source impedance, maximum power 510 is transferred to the tissue being treated. Then, as the output impedance further increases, the power slowly decreases until the power decreases along an asymptotic line 515 of constant voltage.

Figure 6:
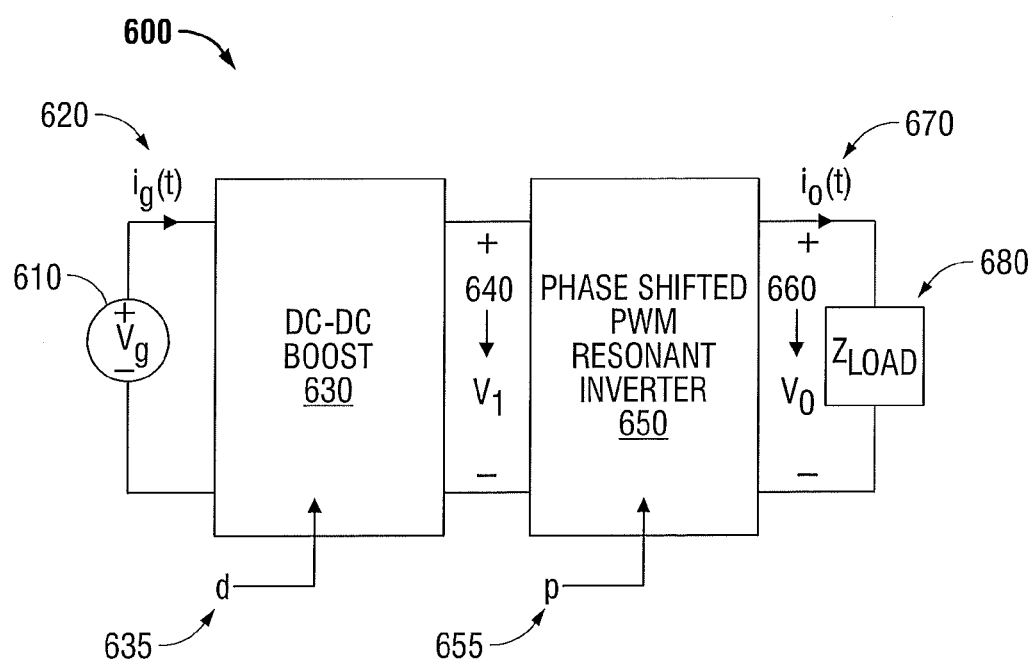
FIG. 6 is a circuit block diagram of generator circuitry according to embodiments of the present disclosure.

As described herein, the systems and methods according to the present disclosure employ a multi-stage output power converter that can achieve a near ideal constant-current, constant-power, and constant-voltage output characteristic by separately selecting the control methodology of each stage of the multi-stage output power converter. FIG. 6 is a circuit block diagram of generator circuitry 600 that may be employed in the electrosurgical generator 102 of FIG. 1. The generator circuitry 600 includes a voltage source 610, a DC-DC boost converter 630, and a phase-shifted (PS) pulse width modulation (PWM) resonant inverter 650.

The voltage source 610 provides direct current $i_g(t)$ 620 to the DC-DC boost converter 630, which steps down or steps up the voltage of the direct current to a desired voltage level $v_1$ 640. Then, the PS-PWM resonant inverter 650 inverts the desired DC voltage $v_1$ 640 provided by the DC-DC boost converter 630 into AC having a voltage and a frequency suitable for treating tissue. The AC voltage $v_o$ output from the PS-PWM resonant inverter 650 is then provided to the tissue load $Z_{load}$ 680.

The controller 260 of FIG. 2 may obtain samples of the DC voltage $v_1$ 640 via sensors 235 and the ADCs 250 and may generate a control signal d 635 to control the DC voltage $v_1$ 640 based on the samples of the DC voltage $v_1$ 640. The controller 260 may also obtain samples of the AC current $i_o(t)$ 670 and AC voltage $v_o$ 660 and may generate another control signal p 655 having a fixed phase to control the PS-PWM resonant inverter 650 based on the samples of the AC current $i_o(t)$ 670 and AC voltage $v_o$ 660.

Figure 7A:
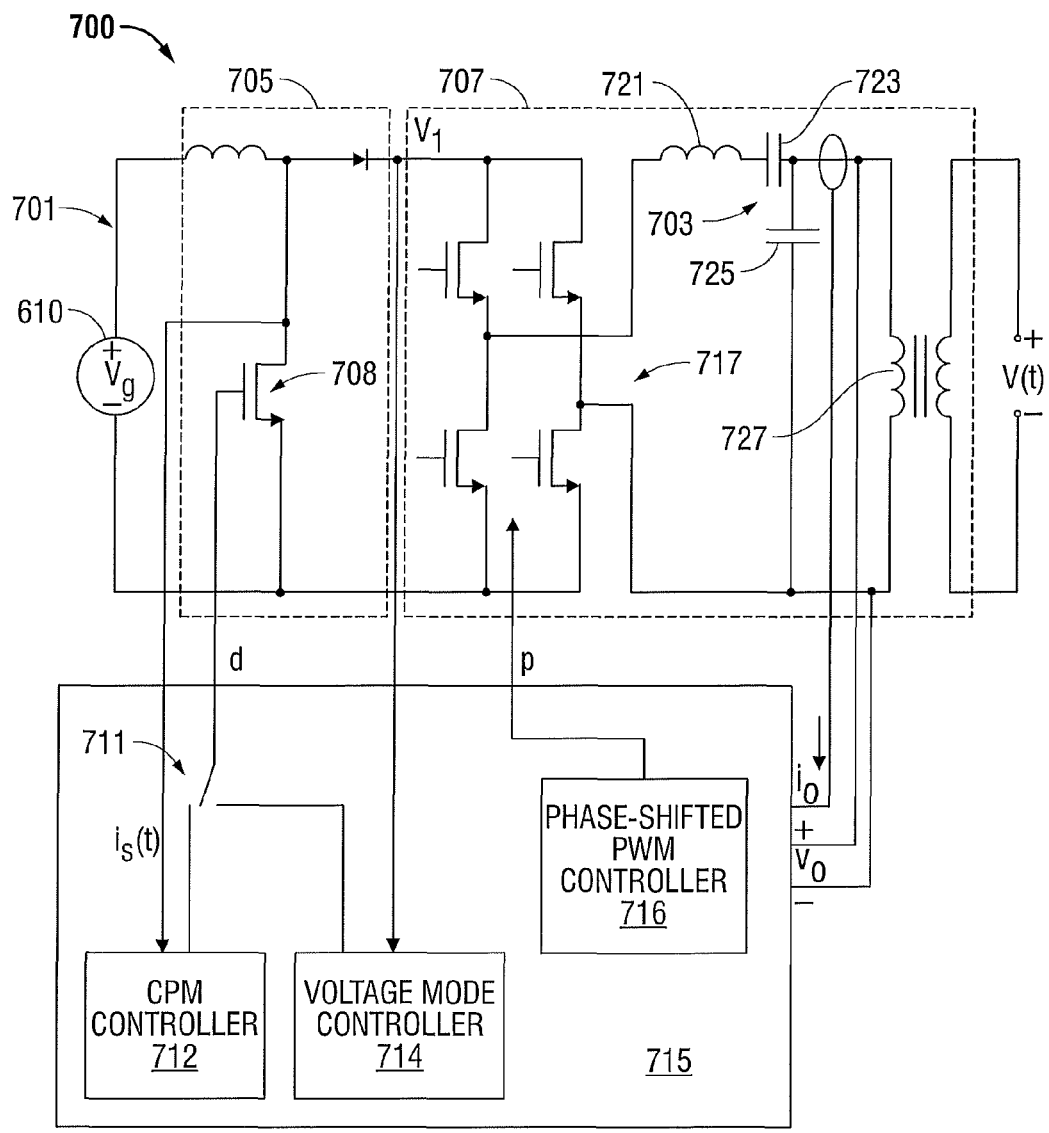
FIG. 7A is a circuit block diagram of generator circuitry according to another embodiment of the present disclosure.

FIG. 7A is a circuit block diagram of generator circuitry 700 including a power converter 701 and a controller 715 for controlling the power converter 701. The power converter 701 includes a boost converter 705 and a PS-PWM resonant inverter 707 connected to the output of the boost converter 705. The PS-PWM resonant inverter 707 includes a series-parallel LCLC resonant tank circuit 703. The series-parallel LCLC resonant tank circuit 703 includes an inductor 721 and a capacitor 723 connected in series with the output of the power converter 701, the primary inductor coil of the transformer 727, and a capacitor 725 connected in parallel with the output of the power converter 701.

The controller 715 includes a CPM controller 712 and a voltage mode controller 714 that control the boost converter 705 with a control signal d having a desired duty cycle, and a phase-shifted PWM controller 716 that controls the PS-PWM resonant inverter 707 with a PWM control signal p having a fixed phase. The controller 715 also includes a switch 711 that switches between the CPM controller 712 and the voltage mode controller 714.

The CPM controller 712, the voltage mode controller 714, and the phase-shifted PWM controller 716 operate according to the desired output characteristic as illustrated in Table 1 below. As described above, the desired output characteristic changes from constant current, to constant power, to constant voltage depending upon the output impedance.

TABLE 1

| Desired Output Characteristic: | Constant Current | Constant Power | Constant Voltage |
|---|---|---|---|
| Control Signal d (provided to the boost converter 705) | Voltage mode control | CPM (current programmed mode) | Voltage mode control |
| Control Signal p (provided to the PS-PWM resonant inverter 707) | Fixed phase $p_1$ | Fixed phase | Fixed phase $p_2$ |

To achieve a constant current output at the beginning of tissue treatment, the controller 715 switches the switch 711 to the voltage mode controller 714, which generates the control signal d having a fixed duty cycle and provides the control signal d to the switch 708 of the DC-DC boost converter 705.

Additionally, the phase-shifted PWM controller 716 generates a PWM control signal p having a first fixed phase $p_1$ and provides it to the H-bridge 717 of the DC-AC PS-PWM resonant inverter 707. The phase-shifted PWM controller 716 varies the duty cycle of the PWM control signal p so that the PS-PWM resonant inverter 707 outputs a constant current.

The voltage mode control involves measuring the output voltage $v_1$ of the DC-DC boost converter 705, feeding the measured output voltage $v_1$ to the voltage mode controller 714, and adjusting the duty cycle of control signal d based on the difference between the measured output voltage $v_1$ and a reference output voltage so that the measured output voltage $v_1$ matches the reference output voltage. The reference output voltage may be set by a user or may be based on reference output voltage values stored in a look-up table. In the voltage control mode, the series impedance 723 of the tank circuit 703 limits the output current.

When the output impedance reaches a first predetermined impedance value, the desired output characteristic changes from constant current to constant power. For the constant power output characteristic, the controller 715 changes the switch 711 to the current programmed mode (CPM) controller 712. The current programmed mode controller 712 varies the duty cycle of the control signal d according to the current programmed mode to maintain a constant power output from the DC-DC boost converter 705. Additionally, the PS-PWM controller 716 generates the control signal p having a fixed phase and a fixed duty cycle, and provides it to the H-bridge 717 of the DC-AC PS-PWM resonant inverter 707.

When the output impedance reaches a second predetermined impedance value, the desired output characteristic changes from constant power to constant voltage. For the constant voltage output characteristic, the controller 715 switches the switch 711 back to the voltage mode controller 714, which varies the duty cycle of the control signal d according to the voltage control mode and provides it to the switch 708 of the DC-DC boost converter 705. In the voltage control mode, the voltage mode controller 714 operates the switch 708 to adjust the voltage to maintain a constant voltage output as the output impedance further changes or increases over time. Additionally, the PS-PWM controller 716 generates the control signal p having a second fixed phase $p_2$ and a fixed duty cycle. In the voltage control mode, the parallel impedance 725 of the tank circuit 703 naturally limits the output voltage.

In embodiments, to switch the boost converter 705 and the PS-PWM resonant inverter 707 between control methods, the output voltage and current may be measured and compared to voltage thresholds set by the control logic, e.g., an FPGA or DSP. The output voltage and current measurements may be rectified by a rectifier and fed to a comparator. A DAC may be connected to the comparator to provide voltages proportional to voltage and current limits. The output of the comparator would then be used to determine the control method of the boost converter 705 and the PS-PWM resonant inverter 707. For example, when the desired output characteristic is constant current and the comparator determines that the measured output voltage has reached the voltage limit, a switch 711 switches from the voltage mode controller 714 to the CPM controller 712.

The boost converter 705 behaves as a constant power source when it is operated in the current program mode. Thus, when the PS-PWM controller 716 controls the PS-PWM resonant inverter 707 with a fixed phase p from the boost converter 705, it can deliver the ideal voltage limit, current limit, and power limit with near deadbeat control.

Figure 7B:
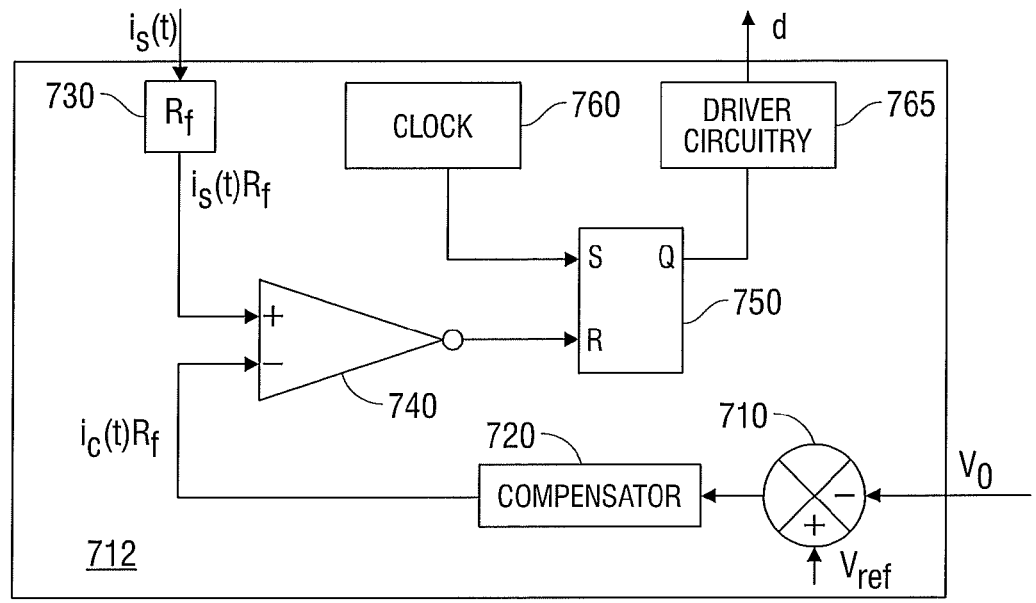
FIG. 7B is a circuit block diagram of a current programmed mode (CPM) controller of the generator circuitry of FIG. 7A.

FIG. 7B is a circuit block diagram of the CPM controller 712 of the controller of FIG. 7A. The CPM controller 712 includes a summing block 710, a compensator 720, a comparator 740 with an inverting output, a current sense resistor 730, a latch 750, a clock 760, and driver circuitry 765 for driving the switch 708 of the boost converter 705. The summing block 710 receives a desired voltage $v_{ref}$ and an output voltage $v_o$ from the resonant inverter 650, which is sensed by a voltage sensor, and determines the difference between the output voltage and the desired voltage. The difference between the output voltage and the desired voltage is then provided to the compensator 720. The compensator 720 outputs a compensator voltage to the comparator 740. The compensator voltage is represented by the product $i_c(t)R_f$, where $i_c(t)$ represents a compensator current and Rf represents the resistance of the current sense resistor 730.

The controller 715 senses the switch current $i_s(t)$ passing through the switch 708 of the boost converter 705 using the current sense resistor 730. The current sense resistor 730 provides a switch voltage $i_s(t)R_f$ to the comparator 740. In some embodiments, the CPM controller 712 may further include a summing block connected between the current sense resistor 730 and the comparator 740. The summing block may add an artificial ramp $i_a(t)R_f$, which may be generated by the clock 760, to the switch voltage $i_s(t)R_f$. The comparator 740 then compares the compensator voltage $i_c(t)R_f$ to the switch voltage $i_s(t)R_f$. If the switch voltage $i_s(t)R_f$ is less than the compensator voltage $i_c(t)R_f$, the comparator 740 sets the latch 750 so that a clock signal generated by the clock 760 is provided to the driver circuitry 765 to drive the switch 708 according to the clock signal. If the switch voltage $i_s(t)R_f$ reaches or exceeds the compensator voltage $i_c(t)R_f$, the comparator 740 outputs a nonzero digital value to the reset input R of the latch 750 to reset the latch 750. When the latch 750 is reset, the latch 750 outputs a zero value to the driver circuitry 765, which sets the control signal d to zero, thereby turning off the switch 708. In this manner, the compensator current $i_c(t)$ acts as a current limit to the switch current $i_s(t)$.

Figure 7C:
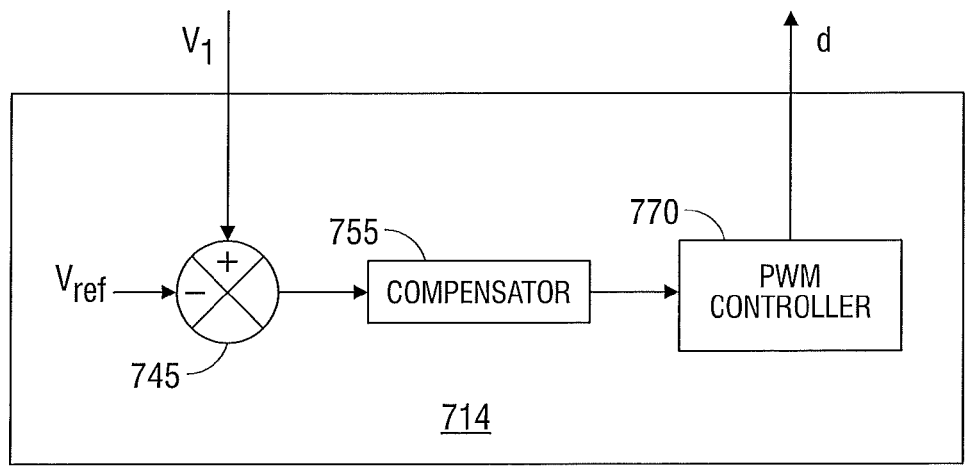
FIG. 7C is a circuit block diagram of a voltage mode controller of the generator circuitry of FIG. 7A.

FIG. 7C is a circuit block diagram of the voltage mode controller 714 of the generator circuitry 700 of FIG. 7A. The voltage mode controller 714 includes a summing block 745, a compensator 755, and a PWM controller 770. The summing block 745 determines the difference between the feedback voltage $v_1$ and reference voltage $v_{ref}$, which, for example, may be the desired voltage for the constant voltage output characteristic. The compensator 755 outputs an error signal based on the output from the summing block 745. Then, the PWM controller 770 varies the duty cycle of the driving signal d based on the error signal output from the compensator 755.

Figure 8:
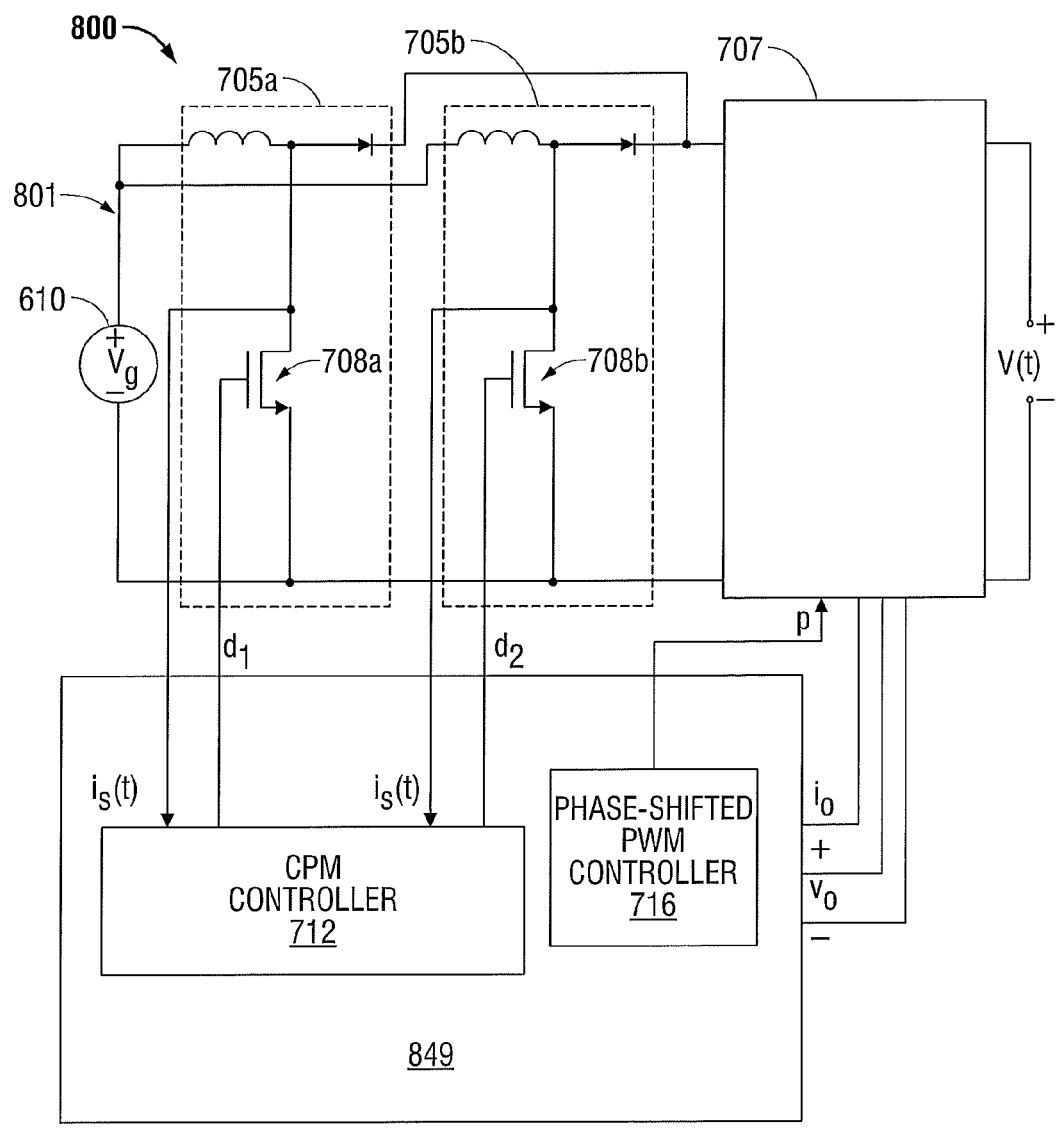
FIG. 8 is a circuit block diagram of generator circuitry according to still another embodiment of the present disclosure.

FIG. 8 is a circuit block diagram of generator circuitry 800 according to another embodiment in which an output power converter 801 includes one or more boost converters 705a and 705b having respective switches 708a and 708b, and the resonant inverter 707 of FIG. 7A. The output power converter 801 is controlled by controller 849 which includes CPM controller 712 for controlling the one or more boost converters 705a and 705b, respectively, and the PS-PWM controller 716 for controlling the PS-PWM resonant inverter 707.

In an embodiment in which the output power converter 801 includes only one CPM controller, e.g., CPM controller 712, the controller 849 operates the output power converter 801 according to the desired output characteristics as shown in Table 2 below.

TABLE 2

| Desired Output Characteristic | Constant Voltage | Constant Current | Constant Power |
|---|---|---|---|
| Control Signal $d_1$ (provided to, e.g., the boost converter 705a) | CPM (current programmed mode) | CPM (current programmed mode) | CPM (current programmed mode) |
| Contro Signal pl (provided to the PS-PWM resonant inverter 707) | Fixed phase | Fixed phase | Fixed phase |

As shown in Table 2, the CPM controller 712 may generate a control signal $d_1$ for the boost converter 705a according to CPM for all the output characteristics, and the PWM controller 716 generates a control signal p for the PS-PWM resonant inverter 707 having a fixed phase for all the output characteristics. The controller 849 may also run a slow control loop to deliver a desired power dosage. At the voltage/current limits, the boost converter 705a would try to deliver constant power to the PS-PWM resonant inverter 707 and the PS-PWM resonant inverter 707 would consume the difference in the power delivered to the load and the power supplied by the boost converter 705a. Essentially, the boost converter 705a and the PS-PWM resonant inverter 707 are run open loop to deliver the ideal output characteristics.

The boost converter 705a may be run at a faster switching frequency compared to the PS-PWM resonant inverter 707, e.g., N-times faster. Thus, during the constant power output characteristic, the output of the PS-PWM resonant inverter 707 would deliver constant power over 1/Nth of a cycle.

The output power converter 801 may include two or more boost converters coupled together in parallel and controlled by two or more corresponding control signals that are shifted in time with respect to each other in a symmetrical way. In the case of two boost converters, e.g., boost converters 705a and 705b, the control signals for the boost converters, e.g., control signals $d_1$ and $d_2$, may have a 180-degree phase difference. In the case of three boost converters, the phase difference between any two of the three corresponding control signals would be 120 degrees. In the case of four boost converters, the phase difference between any two of the four corresponding control signals would be 90 degrees. By increasing the number of boost converters, the generator circuitry 200 may achieve an ideal power versus impedance output characteristic, lower output measurement sampling rates, improved clamping of voltage and current without using active electrical elements, such as an active snubber, and control constant power delivery.

When operating under CPM, each boost converter maintains a constant average power over its own cycle and all the phases deliver an average constant power over their multiphase period. The output power converter topology using two or more boost converters is inherently slower than the single boost stage running at N times the speed of the PS-PWM resonant inverter 707 because the total average power is only constant over an entire multi-phase period. But, the multi-boost converter topology provides lower input voltage and current ripple than the single boost converter topology.

Figure 9:
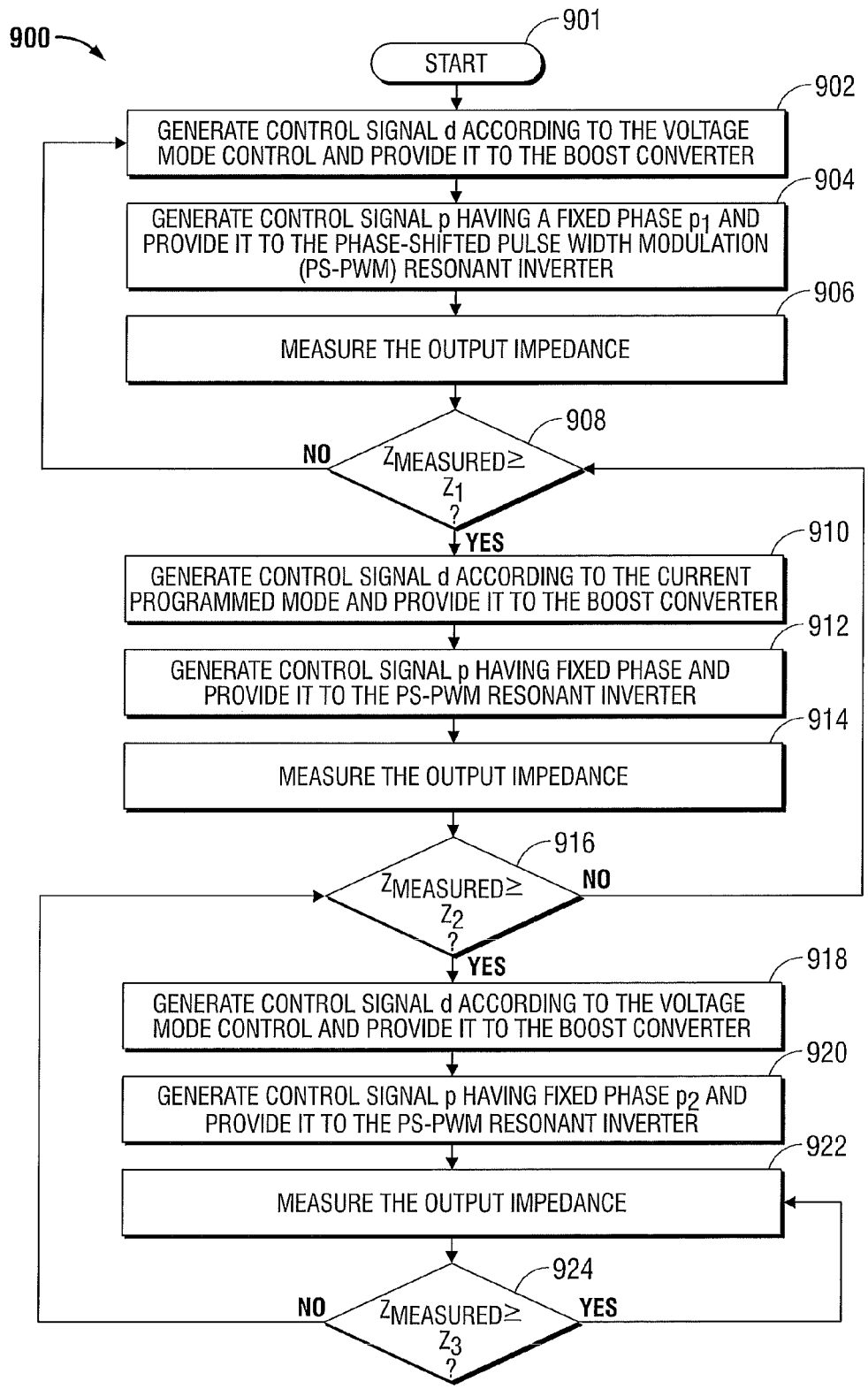
FIG. 9 is a flow diagram illustrating a method of controlling an output power converter according to an embodiment of the present disclosure.

FIG. 9 is a flow diagram illustrating a method 900 of controlling the output power converter of FIG. 7A based on the impedance of the tissue being treated. In this method, the desired output characteristic is changed from constant current, to constant power, and to constant voltage based on the impedance of the tissue being treated. After starting in step 901, the controller 715 operates the output power converter to provide a constant current output characteristic. Specifically, the controller 715 generates a control signal d according to the voltage mode control and a control signal p having a fixed phase $p_1$, and provides them to the boost converter 705 and the phase-shifted pulse width modulation (PS-PWM) resonant inverter 707 in steps 902 and 904, respectively. The controller 715 then measures the impedance of the tissue being treated in step 906. The measured impedance is compared to the first predetermined impedance value $Z_1$ in step 908. If the measured impedance is less than the first predetermined impedance value $Z_1$, steps 902 and 904 are repeated to provide a constant current output characteristic. Otherwise, steps 910 and 912 are performed to provide a constant power output characteristic.

In step 910, a control signal d is generated according to the current programmed mode and is provided to the boost converter 705. In step 912, a control signal p having a fixed phase is generated and provided to the boost converter 705. The controller 715 then measures the impedance of the tissue being treated in step 914. In step 916, the measured impedance is compared to a second predetermined impedance value $Z_2$. If the measured impedance is less than the second predetermined impedance value $Z_2$, the method 900 returns to step 908, and steps 910 and 912 are repeated to provide a constant power output characteristic. Otherwise, steps 918 and 920 are performed to provide a constant voltage output characteristic.

In steps 918 and 920, the controller 715 generates a control signal d according to the voltage mode control and a control signal p having a fixed phase $p_2$, and provides them to the boost converter 705 and the PS-PWM resonant inverter 707, respectively. The controller 715 then measures the impedance of the tissue being treated in step 922. In step 924, the measured impedance is compared to the third predetermined impedance value $Z_3$. If the measured impedance is less than the third predetermined impedance value $Z_3$, the method 900 returns to step 916 and performs steps 918-924 based on the constant voltage output characteristic. Otherwise, the method 900 of controlling the power converter 701 returns to step 922 to continue measuring the output impedance, e.g., the tissue impedance. Since step 922 does not generate control signals, the boost converter and the PS-PWM resonant inverter do not output voltage and current waveforms to the tissue being treated. Nevertheless, the electrosurgical operation does not end until a user turns off a power switch of the electrosurgical generator or terminates supplying power to the electrosurgical generator.

Figure 10:
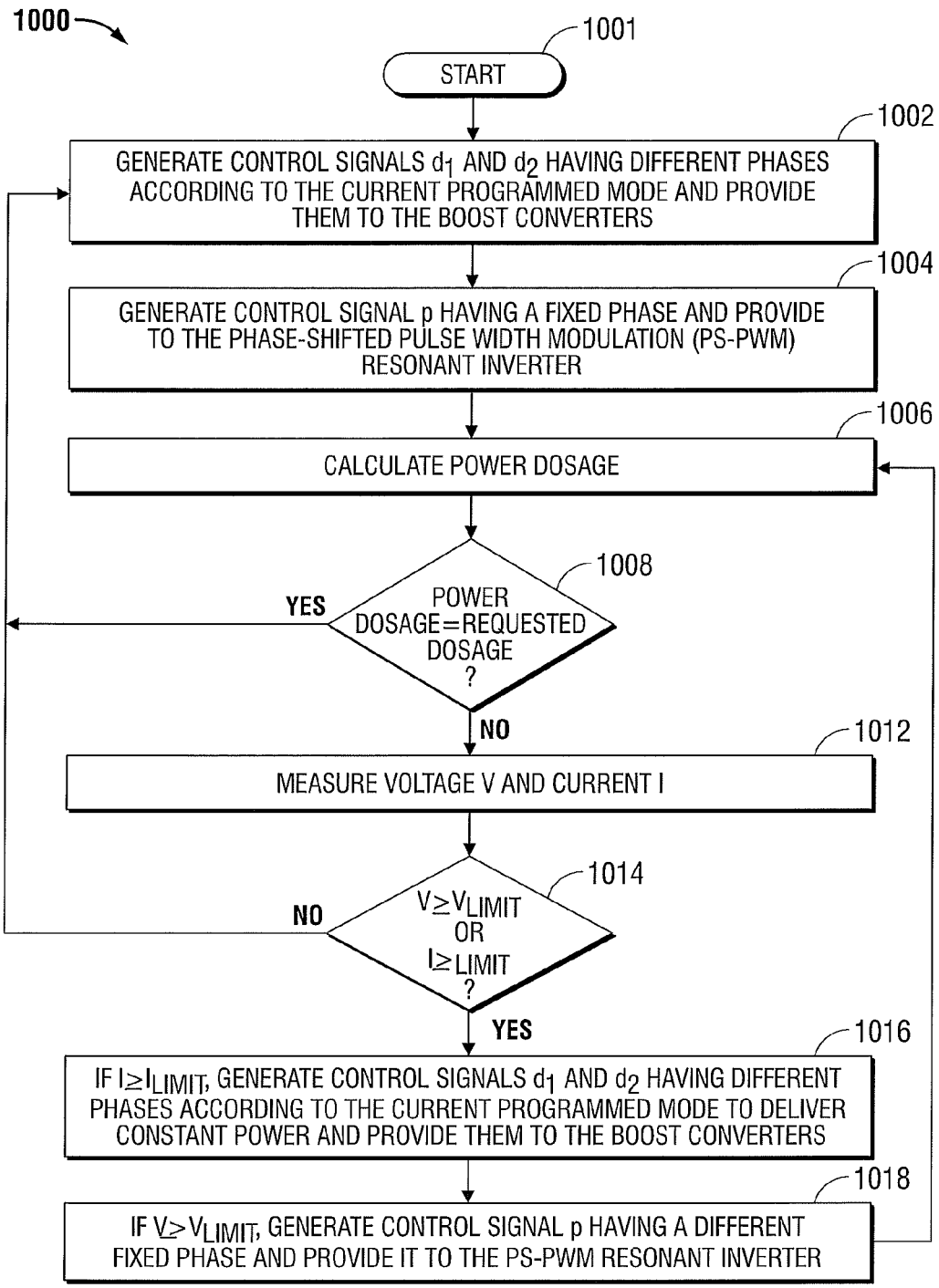
FIG. 10 is a flow diagram illustrating a method of controlling an output power converter according to another embodiment of the present disclosure.

FIG. 10 is a flow diagram illustrating a method 1000 of controlling the output power converter 801 of FIG. 8. As shown in FIG. 8, the controller 849 controls two boost converters 705a and 705b and the PS-PWM resonant inverter 707. After starting in step 1001, the controller 849 generates, in step 1002, two control signals $d_1$ and $d_2$ having different phases according to the current programmed mode and provides them to the two boost converters to control the boost converters 705a and 705b, respectively. In step 1004, the controller 849 generates a control signal p having a fixed phase and provides it to the resonant inverter 707.

In step 1006, the power dosage is calculated and, in step 1008, the power dosage is compared to a requested power dosage. If the power dosage is equal to the requested power dosage, the method 1000 returns to step 1002. If not, voltage and current are measured at the output of the generator circuitry 800, in step 1012. In step 1014, the measured voltage and the measured current are compared to the voltage limit and the current limit, respectively. When the measured voltage and the measured current are less than the voltage limit and the current limit, respectively, the method 1000 returns to step 1002.

In the case where the measured current is greater than or equal to the current limit, the controller 849 generates control signals $d_1$ and $d_2$ having different phases from those of already generated two control signals and provides them to the two boost converters so that a current lower than the current limit is generated, in step 1016. In the case where the measured voltage is greater than or equal to the voltage limit, the controller 849 generates a control signal p having a different fixed phase and provides it to the resonant inverter 707 so that a voltage lower than the voltage limit is generated, in step 1018. Then, the method 1000 returns to step 1006.

Although the illustrative embodiments of the present disclosure have been described herein with reference to the accompanying drawings, it is to be understood that the disclosure is not limited to those precise embodiments, and that various other changes and modification may be effected therein by one skilled in the art without departing from the scope or spirit of the disclosure.

What is claimed is:

1. An electrosurgical generator comprising:
   a power converter coupled to an electrical energy source and configured to generate electrosurgical energy, the power converter including:
      a boost converter configured to convert a first direct current from the electrical energy source to a second direct current; and
      a phase-shifted pulse width modulation (PS-PWM) resonant inverter configured to invert the second direct current to an alternating current;
   a plurality of sensors configured to sense voltage and current waveforms of the generated electrosurgical energy; and
   a controller coupled to the power converter and the plurality of sensors, the controller comprising:
      a signal processor configured to determine a tissue impedance based on the sensed voltage and current waveforms; and
      an output controller configured to select one among a plurality of output characteristics based on the tissue impedance, and to generate a first control signal to control the boost converter and a second control signal to control the PS-PWM resonant inverter, according to the selected output characteristic,
   wherein a switching frequency of the boost converter is greater than a switching frequency of the PS-PWM resonant inverter and the switching frequency of the boost converter is an integer multiple of the switching frequency of the PS-PWM resonant inverter,
   wherein the plurality of output characteristics include a constant current output characteristic, a constant voltage output characteristic, and a constant power output characteristic,
   wherein, when the output characteristic is the constant voltage output characteristic, the output controller generates the second control signal having a first fixed phase and a varying duty cycle, and
   wherein, when the output characteristic is the constant power output characteristic, the output controller generates the second control signal having a second fixed phase, which is different from the first fixed phase, and a fixed duty cycle.

2. The electrosurgical generator according to claim 1, wherein the output controller shifts from the constant current output characteristic to the constant power output characteristic and from the constant power output characteristic to the constant voltage output characteristic based on the tissue impedance.

3. The electrosurgical generator according to claim 1, wherein the output controller selects the constant current output characteristic if the tissue impedance is less than a first predetermined value,
   wherein the output controller selects the constant power output characteristic if the tissue impedance is greater than or equal to the first predetermined value and less than a second predetermined value,
   wherein the output controller selects the constant voltage output characteristic if the tissue impedance is greater than or equal to the second predetermined value and less than a third predetermined value, and
   wherein the first predetermined value is less than the second predetermined value and the second predetermined value is less than the third predetermined value.

4. The electrosurgical generator according to claim 1, wherein, when the output characteristic is the constant voltage output characteristic, the output controller generates the first control signal under a voltage control mode.

5. The electrosurgical generator according to claim 1, wherein, when the output characteristic is the constant current output characteristic, the output controller generates the first control signal under a voltage control mode and generates the second control signal having a third fixed phase.

6. The electrosurgical generator according to claim 1, wherein, when the output characteristic is the constant power output characteristic, the output controller generates the first control signal under a current programmed mode.

7. The electrosurgical generator according to claim 1, wherein, when the output characteristic is any one of the constant voltage output characteristic, the constant current output characteristic, and the constant power output characteristic, the output controller generates the first control signal under a current programmed mode.

8. The electrosurgical generator according to claim 1, wherein the boost converter includes a plurality of boost converters to lower ripples of the voltage and current input to the PS-PWM resonant inverter.

9. The electrosurgical generator according to claim 1, wherein the electrosurgical generator further comprises a plurality of analog-to-digital converters (ADCs) configured to sample the sensed voltage and the sensed current to obtain a predetermined number of samples of each of the sensed voltage and the sensed current, and
   wherein the predetermined number of samples corresponds to an integer multiple of an RF frequency of the sensed voltage and the sensed current.

10. The electrosurgical generator according to claim 1, wherein the plurality of sensors includes a Rogowski coil.

11. The electrosurgical generator according to claim 1, wherein the controller is implemented in a field programmable gate array, an application specific integrated circuit, or a digital signal processor.

12. The electrosurgical generator according to claim 1, wherein the output controller is further configured to select one mode among a plurality of modes based on the output characteristics.

13. The electrosurgical generator according to claim 12, wherein the plurality of modes include a voltage control mode and a current programmed mode.

14. The electrosurgical generator according to claim 12, wherein the output controller generates the first control signal based on the selected mode to control the boost converter.

\* \* \* \* \*